United States Patent
Yokoyama et al.

(10) Patent No.: US 10,283,229 B2
(45) Date of Patent: May 7, 2019

(54) HIGH-ASPECT RATIO STRUCTURE PRODUCTION METHOD, ULTRASONIC PROBE PRODUCTION METHOD USING SAME, AND HIGH-ASPECT RATIO STRUCTURE

(71) Applicant: Konica Minolta, Inc., Tokyo (JP)

(72) Inventors: Mitsuru Yokoyama, Takatsuki (JP); Yuko Yoshida, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 74 days.

(21) Appl. No.: 15/428,262

(22) Filed: Feb. 9, 2017

(65) Prior Publication Data
US 2017/0271039 A1    Sep. 21, 2017

(30) Foreign Application Priority Data
Mar. 15, 2016    (JP) .................. 2016-050408

(51) Int. Cl.
| | |
|---|---|
| *B44C 1/22* | (2006.01) |
| *C25D 11/00* | (2006.01) |
| *G21K 1/06* | (2006.01) |
| *C25D 11/02* | (2006.01) |
| *G01N 29/22* | (2006.01) |
| *G01N 29/24* | (2006.01) |
| *G03F 7/16* | (2006.01) |

(Continued)

(52) U.S. Cl.
CPC ............ *G21K 1/067* (2013.01); *C25D 1/003* (2013.01); *C25D 1/10* (2013.01); *C25D 11/02* (2013.01); *G01N 29/222* (2013.01); *G01N 29/245* (2013.01); *G03F 7/16* (2013.01); *G03F 7/2002* (2013.01); *G03F 7/26* (2013.01); *G03F 7/70408* (2013.01); *G21K 1/025* (2013.01); *H01L 41/183* (2013.01); *H01L 41/333* (2013.01); *G01N 23/20075* (2013.01); *G01N 2291/011* (2013.01); *G21K 1/06* (2013.01); *H01L 41/1876* (2013.01)

(58) Field of Classification Search
None
See application file for complete search history.

(56) References Cited

U.S. PATENT DOCUMENTS

| | | | | |
|---|---|---|---|---|
| 8,895,934 B2* | 11/2014 | Wang | .................. | B81C 1/00619 |
| | | | | 250/363.06 |
| 2002/0109134 A1* | 8/2002 | Iwasaki | .................. | B82Y 10/00 |
| | | | | 257/13 |

(Continued)

FOREIGN PATENT DOCUMENTS

| | | |
|---|---|---|
| JP | 2013124959 A | 6/2013 |
| WO | 2012008118 A1 | 1/2012 |

*Primary Examiner* — Shamim Ahmed
(74) *Attorney, Agent, or Firm* — Lucas & Mercanti, LLP

(57) ABSTRACT

A high-aspect ratio structure production method and an ultrasonic probe production method of the present invention include: forming, in a principal surface of a substrate, a plurality of pores each extending in a direction intersecting the principal surface; plugging, among the plurality of pores, one or more pores formed in a first region; and forming a recess in a second region by a wet etching process. A high-aspect ratio structure includes a grating having a plurality of convex portions, wherein each of the plurality of convex portions is provided with a plugging member plugging a plurality of pores formed therein in a thickness direction of the structure.

8 Claims, 26 Drawing Sheets

(51) Int. Cl.
  *G03F 7/20*   (2006.01)
  *G03F 7/26*   (2006.01)
  *C25D 1/00*   (2006.01)
  *C25D 1/10*   (2006.01)
  *G21K 1/02*   (2006.01)
  *H01L 41/18*  (2006.01)
  *H01L 41/333* (2013.01)
  *G01N 23/20*  (2018.01)
  *H01L 41/187* (2006.01)

(56) References Cited

U.S. PATENT DOCUMENTS

| | | | |
|---|---|---|---|
| 2013/0168253 A1* | 7/2013 | Mardilovich | B81C 1/00031 |
| | | | 205/50 |
| 2013/0177738 A1* | 7/2013 | Mardilovich | B81C 1/00031 |
| | | | 428/141 |
| 2013/0279651 A1* | 10/2013 | Yokoyama | G21K 1/02 |
| | | | 378/36 |
| 2014/0241493 A1* | 8/2014 | Yokoyama | G01N 23/20008 |
| | | | 378/36 |
| 2016/0233002 A1* | 8/2016 | Yokoyama | G21K 1/06 |
| 2017/0040076 A1* | 2/2017 | Yokoyama | B06B 1/0662 |

\* cited by examiner

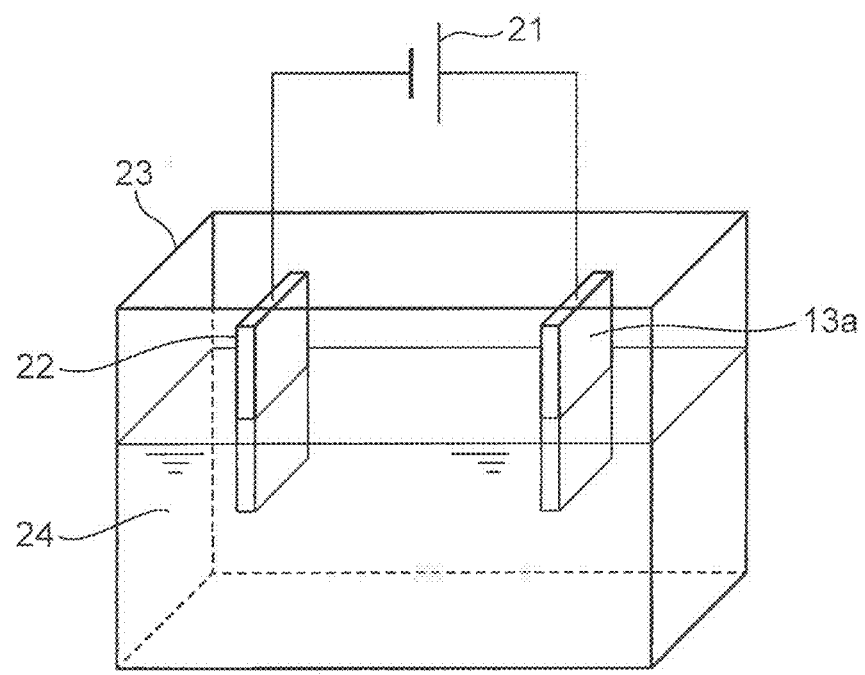

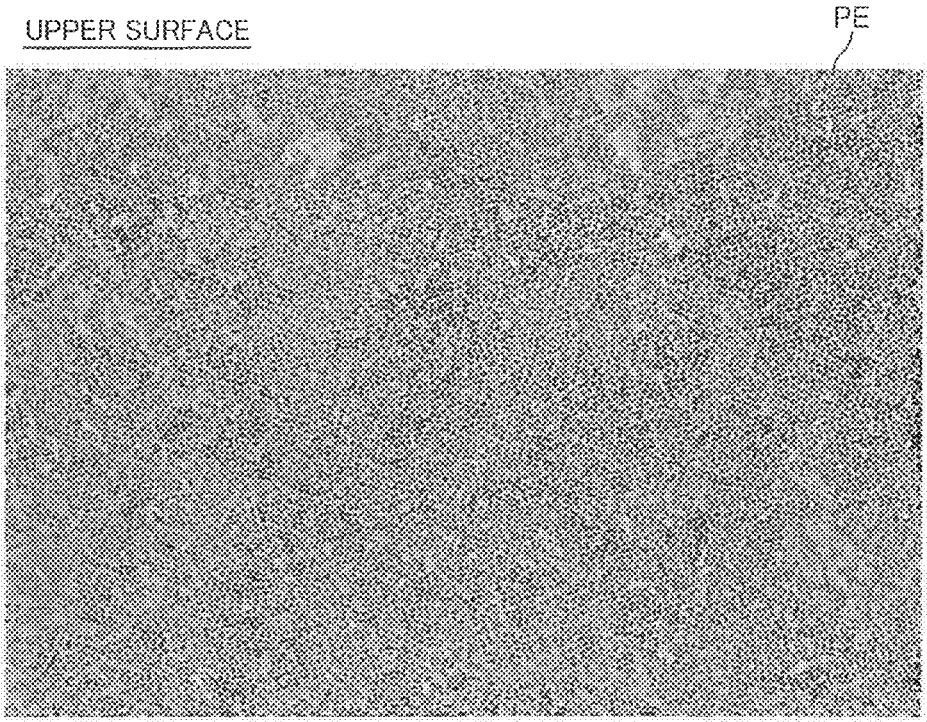

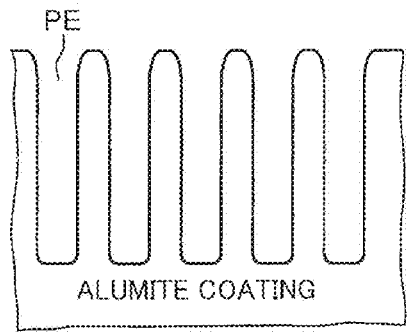
FIG. 8A : BEFORE SEALING PROCESS
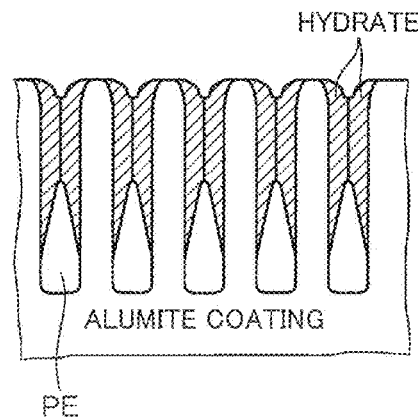
FIG. 8B : AFTER SEALING PROCESS
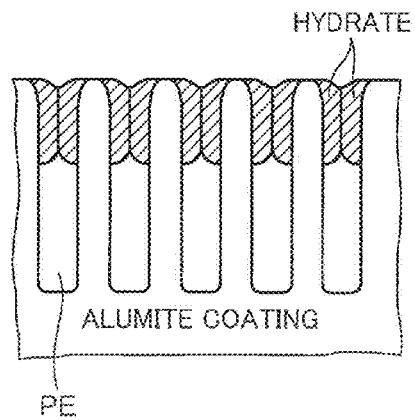
FIG. 8C : AFTER SEALING PROCESS
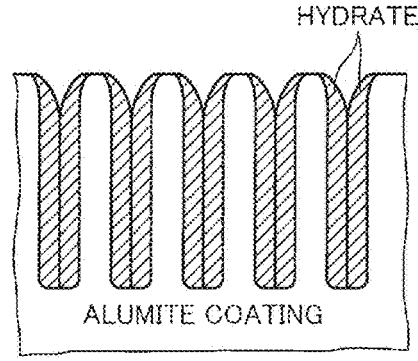
FIG. 8D : AFTER SEALING PROCESS
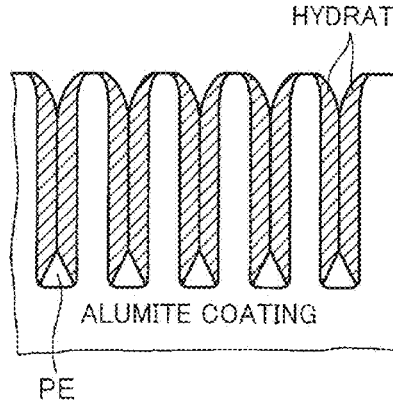
FIG. 8E : AFTER SEALING PROCESS

HIGH-ASPECT RATIO STRUCTURE PRODUCTION METHOD, ULTRASONIC PROBE PRODUCTION METHOD USING SAME, AND HIGH-ASPECT RATIO STRUCTURE

TECHNICAL FIELD

The present invention relates to a high-aspect ratio structure production method, i.e., a method for producing a high-aspect ratio structure having an aspect ratio of 3 or more, such as an X-ray metal grating structure or an ultrasonic probe production mold. The present invention also relates to an ultrasonic probe structure production method, i.e., a method for producing an ultrasonic probe, using the high-aspect ratio structure production method. Further, the present invention relates to such a high-aspect ratio structure.

BACKGROUND ART

For example, an X-ray metal grating structure for receiving X-rays is utilized in various devices, as an element having a large number of parallel periodic structures, and, in recent years, its application to X-ray imaging devices has been attempted. In the field of X-ray imaging devices, from a viewpoint of reduction in exposure dose, great interest has been recently shown in X-ray phase imaging, which is based, for example, on a Talbot interferometer or a Talbot-Lau interferometer. In an X-ray imaging device employing the Talbot-Lau interferometer, three X-ray metal grating structures consisting of a zeroth grating, a first grating and a second grating are used. The zeroth grating is a normal grating utilizable to modify a single X-ray source to a multiple source, i.e., is capable of dividing a flux of X-rays radiated from the single X-ray source, into a plurality of fluxes of X-rays (plurality of X-ray beams) and radiating them therefrom. The first and second gratings are diffraction gratings arranged in such a manner as to be spaced apart from each other by a Talbot distance, and make up the Talbot-Lau interferometer (or Talbot interferometer). In terms of a diffraction process, the diffraction grating can be classified into a transmissive diffraction grating and a reflective diffraction grating, wherein the transmissive diffraction grating includes an amplitude-type diffraction grating (absorptive diffraction grating) light-transmissive substrate, and a phase-type diffraction grating in which a plurality of optical phase-shifting portions are periodically arranged on a light-transmissive substrate.

Such X-ray phase imaging requires an absorptive diffraction grating capable of providing clear contrast between transmission and non-transmission of X-rays having high penetration property, and a phase-type diffraction grating capable of providing clear phase contrast (shift) of X-rays. Thus, there is a need for a high-aspect ratio-structured grating having an extremely high aspect ratio, for example, of 3 or more. For this purpose, there has been proposed a fabrication method using silicon processing created by applying semiconductor processing techniques. As an example, WO 2012/008118A (Literature 1) discloses a production method for a metal grating structure. The metal grating structure production method disclosed in this Literature 1 comprises forming a recess (slit) using a dry etching apparatus, and then burying a metal in the recess.

Meanwhile, the dry etching apparatus is costlier than a wet etching apparatus, assuming that the two apparatuses process isometric workpieces. Thus, in the method disclosed in the Literature 1, the use of the costly dry etching apparatus inevitably leads to an increase in production cost. Particularly, in the case where a large-area substrate having a size equal to or greater than that of an 8-inch wafer is subjected to dry etching, its production cost becomes higher.

Therefore, for performing the processing at lower cost, it is conceivable to utilize a wet etching process. However, in the case where a recess is formed in a substrate by a commonly-used wet etching process, dissolution progresses not only in a depth direction but also in a lateral direction, with respect to an opening of a resist, because a dissolving action of an etching solution is isotropic. For this reason, in the wet etching process, a so-called undercut occurs. As a result, the recess formed by the wet etching process has a side surface inclined with respect to a principal surface of the substrate. Thus, a conventional processing based on the wet etching process has difficulty in forming a recess having a side surface perpendicular to the principal surface.

SUMMARY OF INVENTION

The present invention has been made in view of the above circumstance, and an object thereof is to provide a high-aspect ratio structure production method, i.e., a method for producing a high-aspect ratio structure with a recess having a side surface approximately perpendicular to a principal surface of a substrate by means of wet etching, and an ultrasonic probe structure production method, i.e., a method for producing an ultrasonic probe, using the high-aspect ratio structure production method. It is another object of the present invention to provide such a high-aspect ratio structure.

A high-aspect ratio structure production method and an ultrasonic probe production method include: forming, in a principal surface of a substrate, a plurality of pores each extending in a direction intersecting the principal surface; plugging a part of the plurality of pores in a first region; and forming a recess in a second region having the remaining pores, by a wet etching process. A high-aspect ratio structure includes: a grating having a plurality of convex portions, wherein each of the plurality of convex portions is provided with a plugging member plugging a plurality of pores formed in a thickness direction of the structure.

These and other objects, features and advantages of the present invention will become more apparent upon reading the following detailed description along with the accompanying drawings.

BRIEF DESCRIPTION OF DRAWINGS

FIG. 6 is a diagram illustrating an anodic oxidation process for forming a plurality of pores in a metal substrate.

FIG. 7 is a diagram depicting, as one example, an upper surface of the metal substrate in which a plurality of pores are formed by the anodic oxidation process.

FIGS. 8A-8E is a diagram illustrating a sealing process in a plugging step.

DESCRIPTION OF EMBODIMENTS

Based on the drawings, an embodiment of the present invention will now be described. It should be noted that elements or components assigned with the same reference sign in the figures means that they are the same elements or components, and duplicated descriptions thereof will be appropriately omitted. In this specification, for a generic term, a reference sign without any suffix is assigned thereto, and, for a term meaning an individual element or component, a reference sign with a suffix is assigned thereto.

A high-aspect ratio structure according to one embodiment includes: a substrate; and a grating formed in the substrate, wherein the grating has a plurality of convex portions formed to have a spatial periodicity, and wherein each of the plurality of convex portions is provided with a plugging member plugging a plurality of pores (open-pores) formed therein in a thickness direction of the substrate. Examples of the high-aspect ratio structure include a metal grating structure, more preferably, an X-ray metal grating structure, and an ultrasonic probe production mold. The following description will be made about the X-ray metal grating structure in a more specific manner, and then made about the ultrasonic probe production mold in a more specific manner.

First Embodiment; X-Ray Metal Grating Structure as One Example of High-Aspect Ratio Structure, and Production Method therefor)

Figure 1:
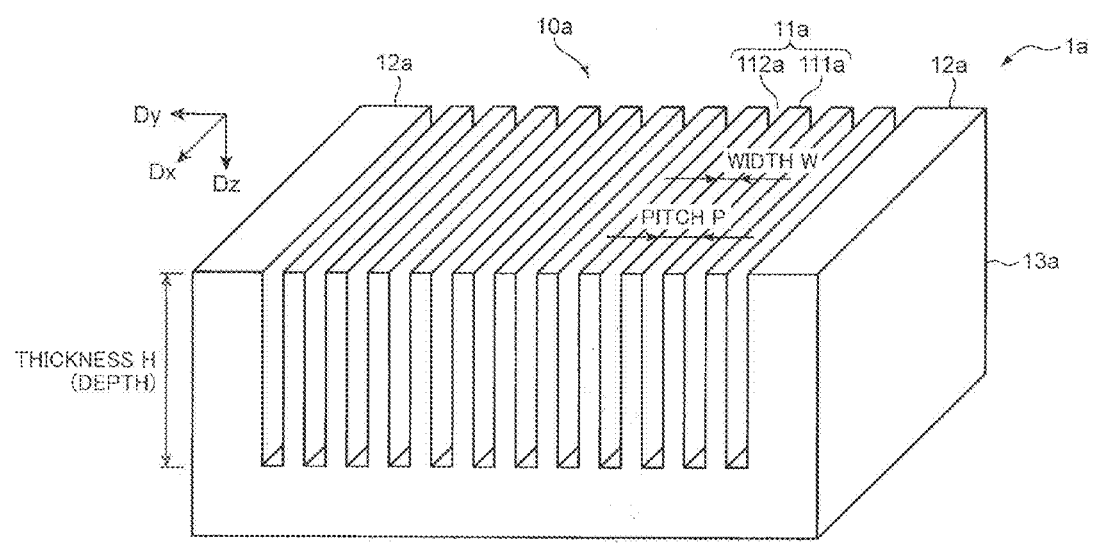
FIG. 1 is a perspective view depicting a configuration of an X-ray metal grating structure according to a first embodiment.

FIG. 1 is a perspective view depicting a configuration of an X-ray metal grating structure according to a first embodiment. The X-ray metal grating structure 1a depicted in FIG. 1 is configured such that it has a grating region 10a and a rim region 12a each provided in an X-ray metal substrate 13a. The grating region 10a is a region in which a grating 11a is formed, and the rim region 12a is provided at a periphery of the grating region 10a to surround the grating region 10a.

Assuming that an orthogonal coordinate system DxDyDz is set as depicted in FIG. 1, the grating 11a comprises: a plurality of X-ray absorptive portions 111a each having a given thickness (depth) H (a length in a direction Dz perpendicular to a grating plane Dx-Dy (a direction normal to the grating plane Dx-Dy)) and linearly extending in a direction Dx as a specific one of three mutually orthogonal directions; a plurality of X-ray transmissive portions 112a each having the given thickness H and linearly extending in the direction Dx, wherein the plurality of X-ray absorptive portions 111a and the plurality of X-ray transmissive portions 112a are alternately arranged parallel to each other. Thus, the plurality of X-ray absorptive portions 111a are arranged at given intervals in a direction Dy orthogonal to the specific direction Dx. In other words, the plurality of X-ray transmissive portions 112a are arranged at given intervals in the direction Dy orthogonal to the specific direction Dx. In this embodiment, the above given interval (pitch) P is set to a constant value. That is, the plurality of X-ray absorptive portions 111a are arranged at even intervals P in the direction Dy orthogonal to the specific direction Dx. In this embodiment, each of the X-ray absorptive portions 111a is a plate-shaped or layer-shaped member along a plane Dx-Dz orthogonal to the plane Dx-Dy, and each of the X-ray transmissive portions 112a is a plate-shaped or layer-shaped space defined along the plane Dx-Dz and between adjacent two of the X-ray absorptive portions 111a.

The plurality of X-ray absorptive portions 111a function to absorb X-rays therein, and the plurality of X-ray transmissive portions 112a function to transmit X-rays therethrough. Therefore, as one embodiment, this X-ray metal grating structure 1a can be utilized as a normal grating having a pitch P sufficiently greater than an X-ray wavelength and thereby free from an interference fringe, such as a zeroth grating in an X-ray Talbot-Lau interferometer. As another embodiment, the X-ray metal grating structure 1a may be configured to function as a diffraction grating by appropriately setting the given interval P depending on the X-ray wavelength. In this case, for example, it can be utilized as a first grating or a second grating in an X-ray Talbot-Lau interferometer or an X-ray Talbot interferometer. The X-ray absorptive portion 111a is formed in an appropriate thickness H so as to sufficiently absorb X-rays, for example, in conformity to a design specification. Generally, X-rays have high penetration property, so that a ratio of the thickness H to a width W in the X-ray absorptive portion 111a (aspect ratio=thickness/width) is set as a high-aspect ratio of 3 or more. In the X-ray absorptive portion 111a, the width W is a length of the X-ray absorptive portion 111a in the direction (width direction) Dy orthogonal to the specific direction (long direction) Dx, and the thickness H is a length of the X-ray absorptive portion 111a in the direction (depth direction) Dz normal to the plane Dx-Dy defined by the specific direction Dx and the direction Dy orthogonal to the specific direction Dx.

In the above description, the X-ray metal grating structure 1a is an absorptive diffraction grating. Differently, the X-ray absorptive portion 111a may be constructed as an X-ray phase-shifting portion having a thickness H adjusted to provide a given phase shift with respect to the X-ray transmissive portion 112a. In this case, the X-ray absorptive portion 111a serves as a phase-type diffraction grating.

This X-ray metal grating structure 1a is produced by a high-aspect ratio structure production method which includes: a pore forming step of forming, in at least one principal surface of a given substrate, a plurality of pores each extending in a direction intersecting the principal surface; a resist layer forming step of forming a resist layer on the principal surface; a patterning step of subjecting the resist layer to patterning, and removing a part of the resist layer after being subjected to the patterning; a plugging step of plugging, among the plurality of pores, one or more pores formed in a first region from which the part of the resist layer has been removed in the patterning step; a resist layer removing step of removing the remaining resist layer left after the patterning step; and a recess forming step of forming, by a wet etching process, a recess in a second region from which the remaining resist layer has been removed in the resist layer removing step. The recess may be composed, for example, a slit groove, in case of a one-dimensional grating structure, or may be composed of a pillar-shaped hole (pillar-shaped opening) or the like in case of a two-dimensional grating structure. A production method for the aforementioned X-ray metal grating structure 1a will be described in detail below, on an assumption that the recess is a slit groove. It should be understood that the same method can be applied in cases where the recess is a recess having any other shape, such as a pillar-shaped hole.

FIGS. 2A to 5D are diagrams illustrating a first production method for the X-ray metal grating structure according to the first embodiment. In FIGS. 2A to 5D, each production step is schematically illustrated based on FIGS. X A and X B as a set, wherein FIG. X A is a sectional view taken in FIG. X B, and FIG. X B is a top view. Further, in FIGS. 2A to 5D, each production step is schematically illustrated based on FIGS. X C and X D as a set, wherein FIG. X C is a sectional view taken in FIG. X D, and FIG. X D is a top view. FIG. 6 is a diagram illustrating an anodic oxidation process for forming a plurality of pores in a metal substrate. FIG. 7 is a diagram depicting, as one example, an upper surface of the metal substrate in which a plurality of pores are formed by the anodic oxidation process. FIGS. 8A to 8E is a diagram illustrating a sealing process in a plugging step, wherein FIG. 8A depicts a state before the sealing process, and each of FIGS. 8B to 8E depicts a state after the sealing process. FIGS. 9A to 9D is a diagram illustrating a process for forming a recess in the metal substrate, in a recess forming step, wherein FIGS. 9A to 9D depict, in this order, a time-series change of the metal substrate, in the recess forming step.

Figure 2A:
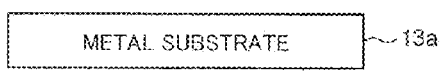
FIGS. 2A-2D is a diagram (I) illustrating a first production method for the X-ray metal grating structure according to the first embodiment.
Figure 2C:
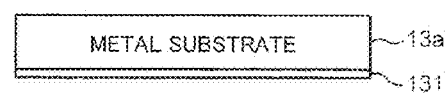
Figure 2B:
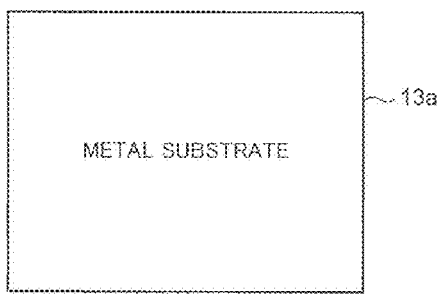

In the first high-aspect ratio structure production method, i.e., a method for producing the X-ray metal grating structure 1a as one example of the high-aspect ratio structure, first of all, a plate-shaped metal substrate 13a is preliminarily prepared in order to produce the X-ray metal grating structure 1a (FIGS. 2A and 2B).

Then, a plurality of pores are formed in at least one principal surface of the metal substrate 13a to extend in a direction intersecting the principal surface, preferably in a direction approximately orthogonal to the principal surface (pore forming step). For this purpose, the metal substrate 13a is formed of a metal (including alloys) capable of allowing a plurality of pores to be formed therein by an anodic oxidation process or an anodic chemical conversion process. As one example, the following description will be made on an assumption that the metal substrate 13a is formed of aluminum.

Figure 2D:
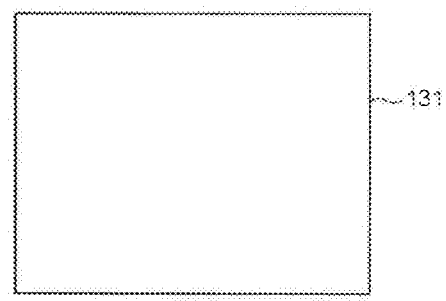

More specifically, in the pore forming step, with a view to forming a plurality of pores only in one principal surface of the metal substrate 13a, a protective film 131 is formed on the other principal surface (a protective film forming substep in the pore forming step; FIGS. 2C and 2D). For example, a quartz (silicon dioxide, $SiO_2$) film 131 is formed as the protective film 131. This quartz film 131 may be formed by one of various film forming processes such as (a chemical vapor deposition (CVD) process and a sputtering process, as heretofore-known commonplace means. As one example, in this embodiment, this quartz film 131 is formed by a plasma CVD process using tetraethoxysilane. More specifically, tetraethoxysilane (TEOS) as one type of organic silane is heated and bubbled by carrier gas to form TEOS gas, and then oxidation gas such as oxygen or ozone and dilution gas such as helium are mixed with the TEOS gas to form raw material gas. Then, the raw material gas is introduced into a plasma CVD apparatus, and a quartz film 131 having a given thickness (e.g., 2 μm) is formed on a surface of the metal substrate 13a inside the CVD apparatus.

It should be noted that the protective film 131 may be formed as a quartz film 131 as mentioned above, but not limited thereto. During implementation of an anodic oxidation process or an anodic chemical conversion process, the protective film 131 functions as a protective film for protecting the metal substrate 13a against a solution for use in the anodic oxidation process or the anodic chemical conversion process. Thus, the protective film 131 may be formed as a film of a dielectric material such as silicon nitride (SiN), or a metal, as long as it has such a function.

Figure 3A:
FIGS. 3A-3D is a diagram (II) illustrating the first production method for the X-ray metal grating structure according to the first embodiment.
Figure 3C:
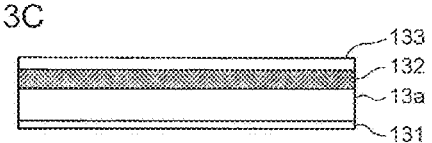
Figure 3B:
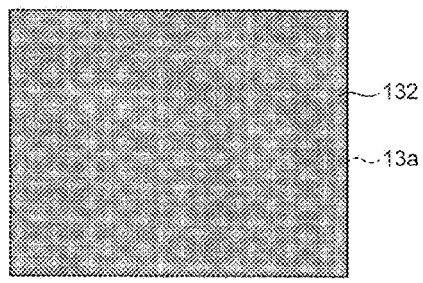
Figure 3D:
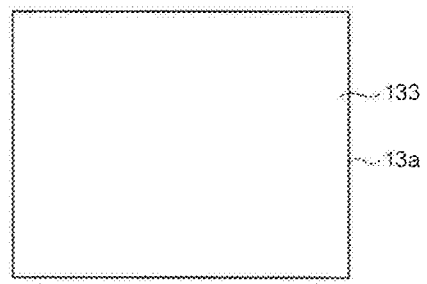

Then, in the pore forming step, a pored layer 132 having a plurality of pores PE is formed in the one principal surface of the metal substrate 13a by an anodic oxidation process or an anodic chemical conversion process (an anodic oxidation substep (anodic chemical conversion substep) in the pore forming step; FIGS. 3A and 3B). For example, in the anodic oxidation substep, a positive electrode of a power source 21 is electrically connected to the metal substrate 13a formed with the protective film in the above manner, and the metal substrate 13a and a cathode electrode 22 connected to a negative electrode of the power source 21 are immersed in an electrolytic solution 24 in a tank 23 storing the electrolytic solution 24, as depicted in FIG. 6. In this case, the cathode electrode 22 and the metal substrate 13a are immersed such that the cathode electrode 22 is opposed to the one principal surface (a surface devoid of the protective film 131) of the metal substrate 13a. The electrolytic solution 24 is preferably an acid solution having a strong oxidative power and capable of dissolving a metal oxide film produced by the anodic oxidation process, e.g., an etchant such as phosphoric acid or oxalic acid. The cathode electrode 22 is preferably formed of a metal insoluble with respect to the electrolytic solution 24, such as gold (Au), platinum (Pt) or carbon (C). In one example, with respect to the metal substrate 13a formed of aluminum, the electrolytic solution 24 is a 0.3 M (mol concentration, mol/l) oxalic acid solution, and the cathode electrode 22 is a titanium plate which is plated with platinum. When applying current, a plurality of pores PE each extending from the one principal surface of the metal substrate 13a toward an inside of the metal substrate 13a are formed. In this embodiment, when applying current, a plurality of pores PE each extending from the one principal surface of the metal substrate 13a in a thickness direction of the metal substrate 13a (Dz direction, the direction perpendicular to the one principal surface) are formed in spaced-apart relation to each other. In one example, by applying a DC voltage of about 20 V between the cathode electrode 22 and the metal substrate 13a for about 10 hours, a plurality of pores each having a diameter $\varphi$ of about 20 nm and a depth H of about 80 μm are formed in spaced-apart relation to each other at an average pitch distance p of about 60 nm. FIG. 7 depicts the one principal surface in this example. In FIG. 7, a photograph taken by a scanning electron microscope (SEM) is presented as a drawing.

Subsequently, a resist layer 133 is formed on the one principal surface of the metal substrate 13a formed with the plurality of pores PE (the resist layer forming step; FIGS. 3A and 3B). For example, the resist layer 133 is formed by attaching a dry film resist on the one principal surface of the metal substrate 13a.

Figure 4A:
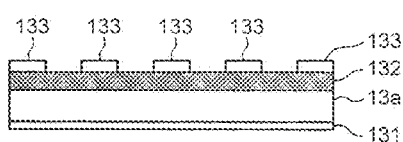
FIGS. 4A-4D is a diagram (III) illustrating the first production method for the X-ray metal grating structure according to the first embodiment.
Figure 4C:
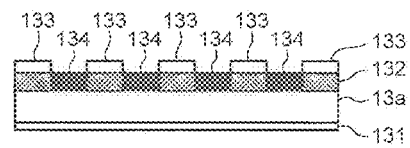
Figure 4B:
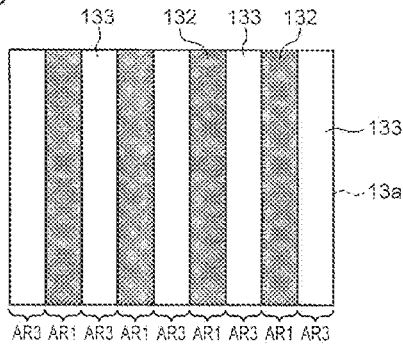

Subsequently, the resist layer 133 is subjected to patterning based on a photolithographic technique, and a part of the resist layer 133 after being subjected to the patterning is removed (the patterning step; FIGS. 4A and 4B). More specifically, a non-depicted lithographic mask is placed on and pressed against the resist layer 133, and ultraviolet light is emitted to the resist layer 133 through the lithographic mask, so that the resist layer 133 is pattern-exposure and developed. Then, a non-exposed portion (or exposed portion) of the resist layer 133 is removed. As a result, for example, a line-and-space pattern in which the resist layer 133 is partially left in a stripe pattern having a pitch (periodic length) of 5.3 μm and a duty ratio of 50% is formed. Thus, the pored layer 132 of the metal substrate 13a has a first region AR1 from which the portion of the resist layer 133 has been removed, and a third region AR3 on which the remaining resist layer 133 is left (disposed).

It should be noted that the resist layer 133 is not limited to a dry film resist, but may be any other suitable resist which includes, but is not limited to, a photoresist. For example, a photoresist is formed on the one principal surface of the metal substrate 13a formed with the plurality of pore PE. Then, after forming a patterned photoresist, a metal film (metal layer) such as chromium (Cr) is formed as a resist layer 133. Then, based on a so-called "liftoff" (removal of the patterned photoresist), the metal film is patterned. Thus, the pored layer 132 of the metal substrate 13a has a first region AR1 from which a part of the metal film as the resist layer 133 has been removed, and a second region AR3 on which a remaining part of the metal film as the resist layer 133 is left (disposed).

Figure 4D:
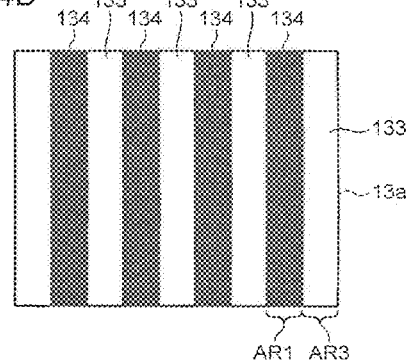

Subsequently, among the plurality of ports PE, one or more pores PE formed in the first region from which the part of the resist layer has been removed in the patterning step are plugged to form a plugged-pore layer 134 (the plugging step; FIGS. 4C and 4D). For example, the one or more pores PE is plugged by a sealing process using a sealing material. More specifically, the metal substrate 13a after the pattering step is immersed in pure water (boiling water) at 98° C., for 1 hour. As a result, in the pores PE in the first region AR1 from which the portion of the resist layer 133 has been removed, as depicted in FIG. 8A, hydrated alumina produced by the boiling water causes volume expansion of alumina, so that at least openings of the pores PR are plugged in various manners as depicted in FIGS. 8B to 8E. More preferably, each of the entire pores PE is filled with hydrated alumina. On the other hand, in one or more pores PE in the third region AR3 on which the remaining resist layer 133 is left (disposed), the resist layer 133 prevents the boiling water from entering the pores PE, so that the pores PE are not plugged.

The sealing process is not limited to the above pure boiling water method using boiling water, but may be any other suitable method, such as a nickel acetate method using a sealing material, e.g., Top-Seal H298 produced by Okuno Chemical Industries Co., Ltd, as presented in

TABLE 1

Table 1.

| CONDITIONS | STEAM METHOD | PURE BOILING WATER METHOD | NICKEL ACETATE METHOD | DICHROMATIC ACID METHOD | SODIUM SILICATE METHOD |
|---|---|---|---|---|---|
| TREATMENT BATH | PRESSURIZED STEAM | PURE WATER | NICKEL ACETATE 5~5.8 g/l COBALT ACETATE 1 g/l BORIC ACID 8~84 g/l | AMMONIUM DICHROMATE 15 g/l SODIUM CARBONATE 4 g/l | SODIUM SILICATE PROCESS |
| pH | — | 6~9 | 5~6 | 6.5~7.5 | — |
| TEMPERATURE (° C.) | (2~5 kg cm$^2$) | 90~100 | 70~90 | 90~95 | 90~100 |
| TIME (min) | 15~30 | 15~30 | 15~20 | 2~10 | 20~30 |

Figure 5A:
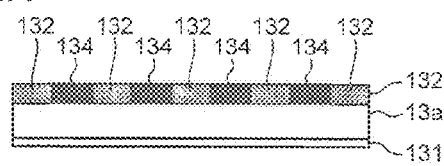
FIGS. 5A-5D is a diagram (IV) illustrating the first production method for the X-ray metal grating structure according to the first embodiment.
Figure 5C:
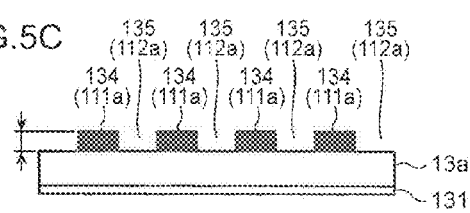
Figure 5B:
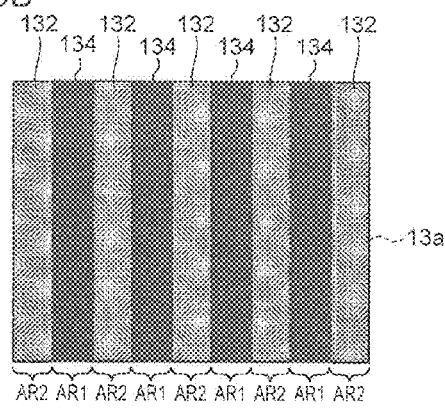

Subsequently, the remaining resist layer 133 left on the third region AR 3 after the patterning step is removed (the resist layer removing step; FIGS. 5A and 5B). For example, the remaining resist layer 133 left after the patterning step is removed using a remover solution exclusively for dry film.

As a result, as depicted in FIGS. 5A and 5B, the one principal surface of the metal substrate 13a has a second region AR2 composed of the pored layer 132 having one or more pores PE whose openings are not plugged (in this embodiment, having one or more pores PE which are not sealed), and the first region AR1 composed of the plugged-pore layer 134 having one or more pores PE whose openings are plugged (in this embodiment, having one or more pores PE which are sealed). In this embodiment, the second region AR2 composed of the pored layer 132 and the first region AR1 composed of the plugged-pore layer 134 are alternately arranged at a periodic pitch of 5.3 μm.

Figure 5D:
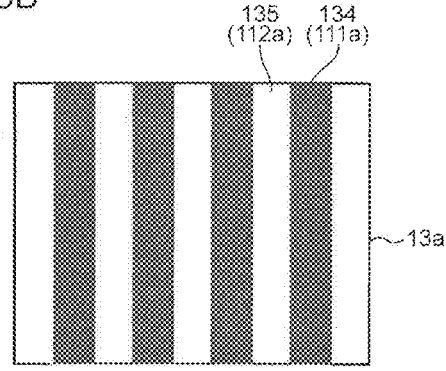
Figure 9A:
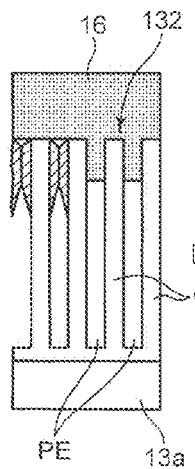
FIGS. 9A-9D is a diagram illustrating a process for forming a recess in the metal substrate, in a recess forming step.
Figure 9B:
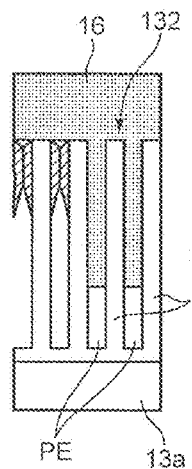
Figure 9C:
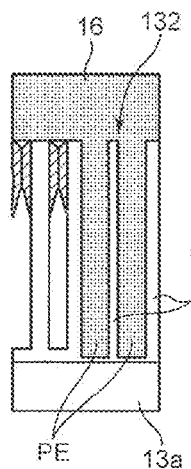
Figure 9D:
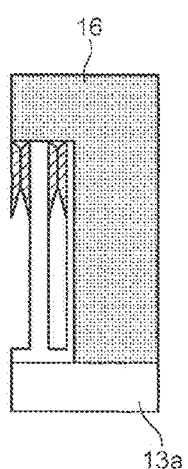

Subsequently, by a wet etching process, a recess 135 is formed in the second region composed of the pored layer 132 from which the remaining resist layer 133 has been removed in the resist layer removing step (the recess forming step; FIGS. 5C and 5D). More specifically, the metal substrate 13a after the resist layer removing step is immersed in a 5 vol % phosphoric acid solution (etchant) 16 and left uncontrolled for 240 minutes. Within several seconds to several minutes after the immersion of the metal substrate 13a, the phosphoric acid solution 16 gradually enters into the pores PE of the pored layer 132 exposed by the resist layer removing step, as depicted in FIGS. 9A, 9B, and 9C in this order. Then, the phosphoric acid solution 16 isotropically etches and dissolves partition walls CW between adjacent ones of the pores PE, by taking all of the remaining time (about 240 minutes), as depicted in FIG. 9D. As a result, a recess 135 is formed in the second region AR2 of the metal substrate 13a.

In this case, based on a preliminarily experiment using a sample, a phosphoric acid concentration of the phosphoric acid solution 16 is set such that a reaching time required for the phosphoric acid solution 16 entering from the openings of the pores PE to reach bottoms of the pores PE becomes less than a dissolving time required for the phosphoric acid solution 16 to dissolve the partition walls CW formed between adjacent ones of the pores PE, preferably, by two digits or more ((the reaching time required for the phosphoric acid solution 16 entering from the openings of the pores PE to reach bottoms of the pores PE)<(the dissolving time required for the phosphoric acid solution 16 to dissolve the partition walls CW formed between adjacent ones of the pores PE), more preferably, (the reaching time required for the phosphoric acid solution 16 entering from the openings of the pores PE to reach the bottoms of the pores PE)≤(the dissolving time required for the phosphoric acid solution 16 to dissolve the partition walls CW formed between adjacent ones of the pores PE)/100). Thus, at a time when each of the partition walls CW is dissolved from each side thereof by 20 nm (one-half of an original wall thickness of the partition wall) and all of the partition walls CW in the second region AR2 disappear, a partition wall CW adjacent to the second region AR2, in the first region AR1, must still have a thickness of 20 nm which is one-half of the original wall thickness thereof. Even if the etching undesirably progresses to cause the partition wall CW adjacent to the second region AR2 to disappear, the width of the recess 135 is increased only by the average pitch distance between adjacent ones of the pores PE.

Through the above production steps, the first region AR1 composed of the plugged-pore layer 134 is formed as the X-ray absorptive portion 111a (or X-ray phase-shifting portion) of the grating 11a, and the recess 135 is formed as the X-ray transmissive portion 112a, so that the X-ray metal grating structure 1a having the configuration depicted in FIG. 1 is produced.

Figure 26A:
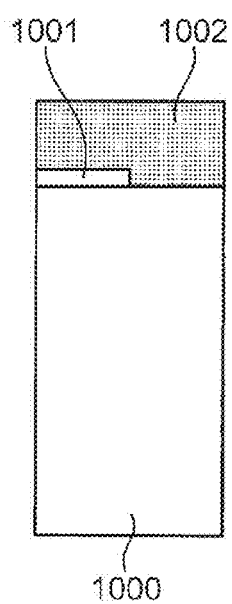
FIGS. 26A-26C is a diagram illustrating a conventional process for fabricating a grating by a wet etching process.
Figure 26B:
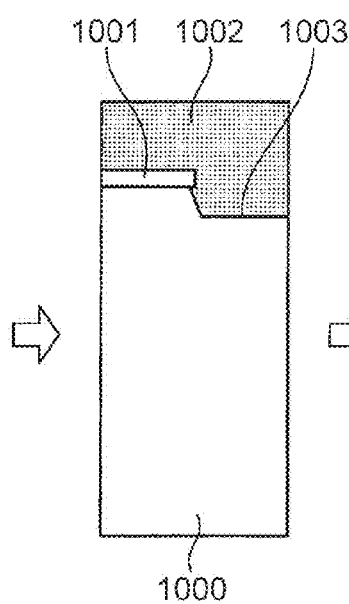
Figure 26C:
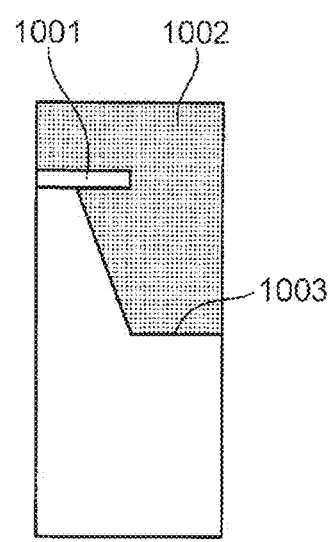

As depicted in FIGS. 26A and 26B, in a conventional commonly-used wet etching process, when a region other than a recess-forming region in one principal surface of a substrate 1000 in which a recess is to be formed is covered by a resist 1001, and then the substrate 1000 is immersed in an etchant 1002 having a function of dissolving the substrate 1000, to dissolve a portion of the substrate 1000 which is not covered by the resist 1001, according to a patterning technique such as photolithography, the etchant flows around the side of a lower surface of the resist 1001 because the dissolving function of the etchant 1002 is generally isotropic, thereby causing an undercut phenomenon, resulting in a recess 1003 having a side surface inclined with respect to the one principal surface. On the other hand, in the first production method for the high-aspect ratio structure according to the first embodiment, during the wet etching process, the resist layer 133 has already been entirely removed, wherein the one or more pores PE formed in the first region AR1 to be still left after the wet etching process are plugged, and the one or more pores PE formed in the second region AR2 from which the remaining resist layer has been removed after the plugging step are kept in an open state. Thus, even when the wet etching process is performed, the undercut phenomenon due to the resist layer 133 never occurs, and an etchant can reach the bottoms of the pores PE in the second region AR2, while dissolving the partition walls formed between adjacent ones of the pores PE. Each of the pores PE extends in the thickness direction of the metal substrate 13a. For example, it is formed to have a relatively long length of several ten to several hundred micron meter by an anodic oxidation process. Thus, the recess 135 can be formed at a high aspect ratio, for example, of 3 or more. Therefore, the first high-aspect ratio structure production method makes it possible to preferably use a wet etching process and produce a high-aspect ratio structure (in the first embodiment, the X-ray metal grating structure 1a) with the recess 135 having a side surface approximately perpendicular to the principal surface of the metal substrate 13a by the wet etching process.

In addition, in the first embodiment, an anodic oxidation process is used in the pore forming step. Thus, the first high-aspect ratio structure production method makes it possible to easily form, in the one principal surface of the metal substrate 13a, a plurality of pores PE perpendicular to the one principal surface (a spreading plane of the one principal surface).

Figure 10:
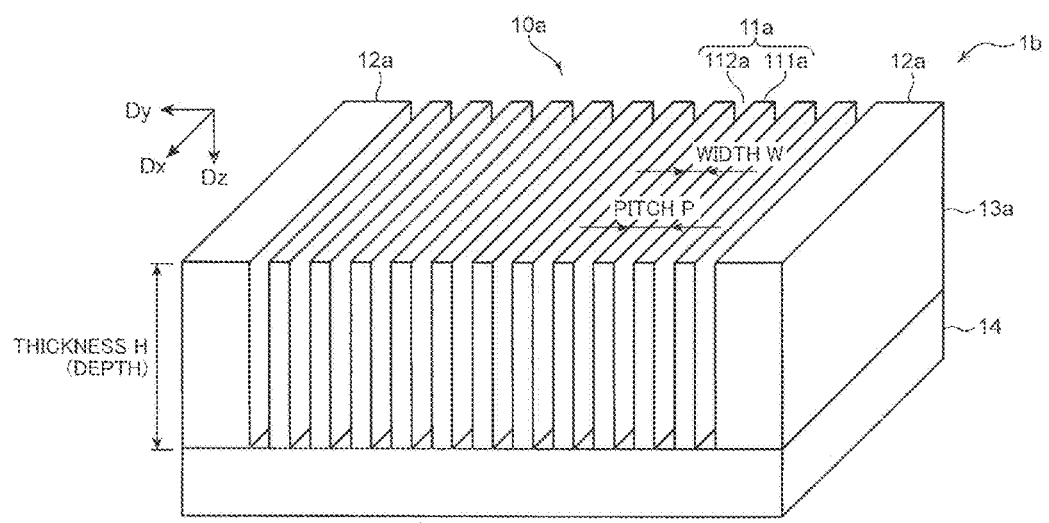
FIG. 10 is a perspective view depicting a configuration of an X-ray metal grating structure as a modification of the first embodiment.
Figure 11A:
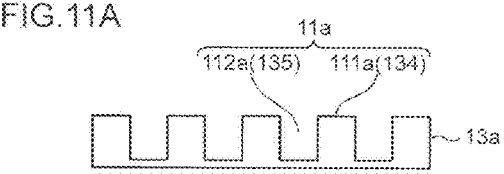
FIGS. 11A-11D is a diagram illustrating a second production method for the X-ray metal grating structure as the modification of the first embodiment.
Figure 11B:
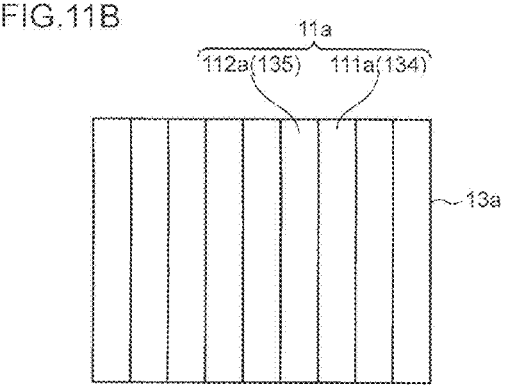
Figure 11C:
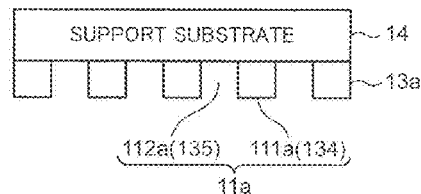
Figure 11D:
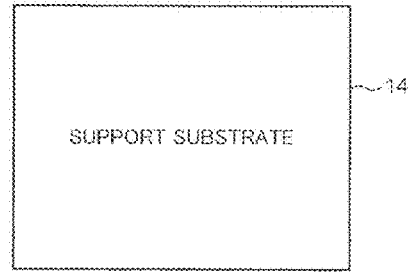

In the first embodiment, the recess (X-ray transmissive portion 112a) may be a through-hole penetrating through the metal substrate 13a in the thickness direction of the metal substrate 13a. An X-ray metal grating structure 1b having a recess (X-ray transmissive portion 112a) composed of such a through-hole, as a modification of the first embodiment, is produced by implementing the following steps in addition to the aforementioned steps. FIG. 10 is a perspective view depicting a configuration of the X-ray metal grating structure as the modification of the first embodiment. FIGS. 11A-11D is a diagram illustrating a second production method for the X-ray metal grating structure as the modification of the first embodiment. In FIGS. 11A to 11D, each production step is schematically illustrated based on FIGS. 11A and 11B as a set, and FIGS. 11C and 11D as a set, wherein FIG. 11A and FIG. 11B are, respectively, a sectional view taken in FIG. 11B, and a top view, and FIG. 11C and FIG. 11D are, respectively, a sectional view taken in FIG. 11D, and a top view.

As described with reference to FIG. 1, in the X-ray metal grating structure 1a according to the first embodiment, the grating region 10a formed with the grating 11a, and the rim region 12a surrounding the grating region 10a, are integrally formed in the metal substrate 13a. On the other hand, in the X-ray metal grating structure 1b as the modification of the first embodiment, a grating region 10a formed with a grating 11a, and a rim region 12a surrounding the grating region 10a, are disposed on one principle surface of a support substrate 14, as depicted in FIG. 10. In the X-ray metal grating structure 1b as the modification of the first embodiment, an X-ray transmissive portion 112a penetrates through a metal substrate 13a in a thickness direction (Dz direction) of the metal substrate 13a, so that a bottom of the X-ray transmissive portion 112a is defined by the one principal surface (a partial region of the one principal surface) of the support substrate 14. Except for this point, the grating region 10a formed with the grating 11a and the rim region 12a in the X-ray metal grating structure 1b as this modification are the same, respectively, as the grating region 10a formed with the grating 11a and the rim region 12a in the X-ray metal grating structure 1a according to the first embodiment. Therefore, descriptions thereof will be omitted.

In the production method for the X-ray metal grating structure 1b as the modification depicted in FIG. 10, after the recess forming step depicted in FIGS. 5C and 5D, the protective film 131 (in the above example, the quartz film 131) is dissolved and removed using a dissolving solution or the like suitable for a material of the protective film 131 (FIGS. 11A and 11B; a protective film removing step).

Subsequently, for example, using an adhesive or the like, the support substrate 14 is fixed to one principal surface of the metal substrate 13a on the side of which the recess 135 (112a) is opened, and then the other principal surface of the metal substrate 13a on the side of which the recess 135 is closed is subjected to cutting such as grinding, until it reaches the recess 135 and enables the recess 135 to be formed as a through-hole, (FIGS. 11C and 11D; a through-hole forming step). The support substrate 14 is a plate-shaped member for supporting the grating region 10a and the frame region 12a, and formed of a material having a high X-ray transmissibility, e.g., a resin material such as acrylic resin. In this way, the X-ray metal grating structure 1b having the configuration depicted in FIG. 10 is produced.

In the second production method for the X-ray metal grating structure 1b, the recess 135 (X-ray transmissive portion 112a) is a through-hole, so that a member forming a bottom of the recesses 135 (X-ray transmissive portion 112a) can be eliminate. This makes it possible to produce a higher-performance X-ray metal grating structure 1b. That is, in this example, an X-ray metal grating structure 1b having a high transmittance can be produced.

Next, another embodiment of the present invention will be described.

(Second Embodiment; X-Ray Metal Grating Structure as Another Example of High-Aspect Ratio Structure, and Production Method therefor)

In the first embodiment, the X-ray metal grating structure 1b is configured such that the recess 135 which is a plate-shaped or layer-shaped member along a plane Dx-Dz functions as the X-ray transmissive portion 112a, and the plugged-pore layer 134 functions as the X-ray absorptive portion 111a (or X-ray phase-shifting portion), whereas, in the second embodiment, an X-ray metal grating structure 1c is configured such that an X-ray absorptive material capable of absorbing X-rays is buried in the recess 135, wherein the recess 135 having the X-ray absorptive material buried therein functions as with the X-ray absorptive portion 111a (or X-ray phase-shifting portion), and the plugged-pore layer 134 functions as with the X-ray transmissive portion 112a.

Figure 12:
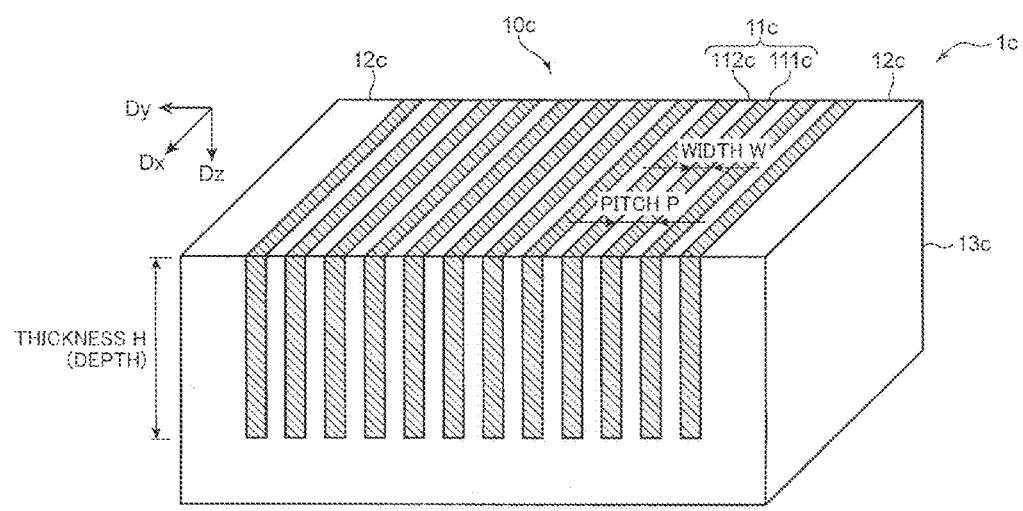
FIG. 12 is a perspective view depicting a configuration of an X-ray metal grating structure according to a second embodiment.
Figure 13A:
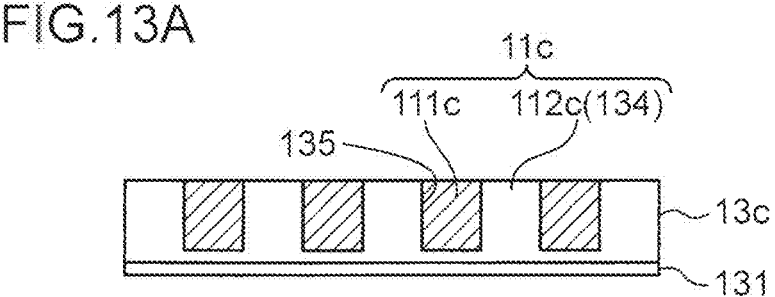
FIGS. 13A and 13B is a diagram illustrating a third production method for the X-ray metal grating structure according to the second embodiment.
Figure 13B:
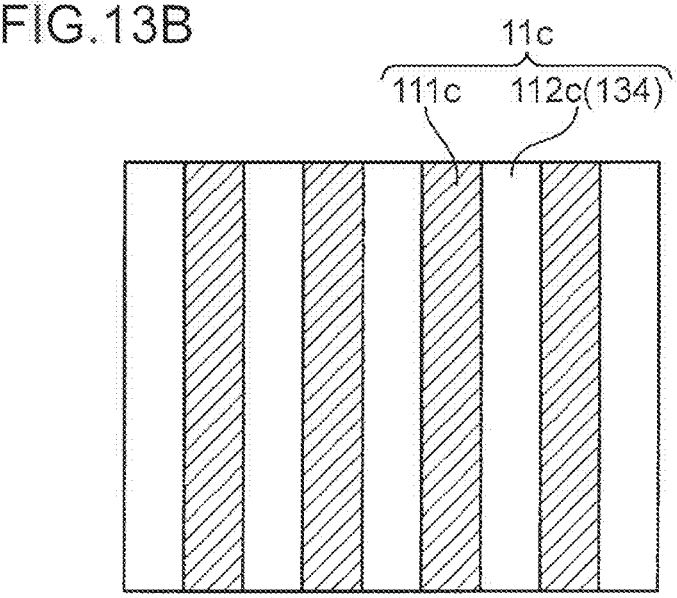

FIG. 12 is a perspective view depicting a configuration of the X-ray metal grating structure according to the second embodiment. FIGS. 13A and 13B is a diagram illustrating a third production method for the X-ray metal grating structure according to the second embodiment. In FIGS. 13A and 13B, each production step is schematically illustrated based on FIGS. 13A and 13B as a set, wherein FIG. 13A is a sectional view taken in FIG. 13B, and FIG. 13B is a top view.

As depicted in FIG. 12, the X-ray metal grating structure 1c according to the second embodiment is configured such that it has a grating region 10c and a rim region 12c each provided in an X-ray metal substrate 13c. The grating region 10c is a region in which a grating 11c is formed, and the rim region 12c is provided at a periphery of the grating region 10c to surround the grating region 10c.

In the X-ray metal grating structure 1a according to the first embodiment, the X-ray absorptive portion 111a is a plate-shaped or layer-shaped member (the plugged-pore layer 134) along the plane Dx-Dz, fabricated from the metal substrate 13a by implementing the steps depicted in FIGS. 2A to 5D, and the X-ray transmissive portion 112a is a plate-shaped or layer-shaped space (slit groove) along the plane Dx-Dz, fabricated from the metal substrate 13a by implementing the steps depicted in FIGS. 2A to 5D. On the other hand, in the X-ray metal grating structure 1c according to the second embodiment, an X-ray absorptive portion 111c is a member made of a metal material having a high X-ray absorptive property buried in a plate-shaped or layer-shaped space (slit groove) along the plane Dx-Dz, fabricated from the metal substrate 13c by implementing aforementioned steps, and an X-ray transmissive portion 112c is a plate-shaped or layer-shaped member along the plane Dx-Dz, fabricated from the metal substrate 13c by implementing the aftermentioned steps. Except for this point, the grating region 10c formed with the grating 11c, and the rim region 12c, in the X-ray metal grating structure 1c according to the second embodiment are the same, respectively, as the grating region 10a formed with the grating 11a, and the rim region 12a, in the X-ray metal grating structure 1a according to the first embodiment. Therefore, descriptions thereof will be omitted. The X-ray absorptive portion 111c and the X-ray transmissive portion 112c in the grating 11c correspond, respectively, to the X-ray absorptive portion 111a and the X-ray transmissive portion 112a in the grating 11a.

This X-ray metal grating structure 1c is produced by a method including: the pore forming step, the resist layer forming step, the patterning step, the plugging step, the resist layer removing step and the recess forming step each described in connection with the first embodiment; and an X-ray absorptive material burying step of burying an X-ray absorptive material capable of absorbing X-rays, in the recess. The recess may be composed, for example, a slit groove, in case of a one-dimensional grating structure, or may be composed of a pillar-shaped hole (pillar-shaped opening) or the like in case of a two-dimensional grating structure. A production method for the aforementioned X-ray metal grating structure 1a will be described in detail below, on an assumption that the recess is a slit groove. It should be understood that the same method can be applied in cases where the recess is a recess having any other shape, such as a pillar-shaped hole.

For producing the X-ray metal grating structure 1c according to the second embodiment, the pore forming step, the resist layer forming step, the patterning step, the plugging step, the resist layer removing step and the recess forming step in the method for producing the X-ray metal grating structure 1a according to the first embodiment are implemented in the same manner.

Then, assuming that a property in terms of X-rays in a first metal forming the metal substrate 13c is a first property, after completion of the recess forming step, a second metal having a second property in terms of X-rays which is different from the first property is buried in the recess 135 (a metal burying step (in this embodiment, an X-ray absorptive material burying step); FIGS. 13A and 13B). In the second embodiment, the metal substrate 13c is formed of a metal having an X-ray transmissive property to serve as the first metal (in this embodiment, aluminum), and thus the second metal is a metal having an X-ray absorptive property. Examples of the second metal having an X-ray absorptive property include a metal element having a relatively heavy atomic weight, and a noble metal, more specifically, include gold (Au), platinum (Pt), rhodium (Rh), ruthenium (Ru) and iridium (Ir).

More specifically, a plurality of metal particles are buried from an opening of the recess 135 into the recess 135 by means of vibration (vibration process). More specifically, the metal substrate 13c fabricated through the above steps is fixed to a bottom surface of a container, and a solid gold power having a tap density of about 8 g/cc and a particle size of about 0.2 to 1.0 μm is put in the container. Then, vibration of about 10 Hz is applied to the container by a vibration generator for generating vibration, so that the metal substrate 13c is vibrated through the container. As a result, gold is buried in the slit groove-shaped recess 135 to form the X-ray absorptive portion 111c.

A means for implementing of realizing the metal burying step is not limited to the vibration process, but may be any other suitable process capable of burying the second metal in the recess 135. For example, the means for implementing the metal burying step may be a supercritical fluid chemical deposition process. This supercritical fluid chemical deposition process is a heretofore-known technique disclosed, for example, in JP 2013-124959A, wherein the process generally includes: a supercritical fluid forming step of causing a solvent to undergo a phase transition to a supercritical fluid; a dissolving step of dissolving, as a solute, a metal compound containing an element of the second metal, in a solvent consisting of the supercritical fluid; an introduction step of introducing the metal compound dissolved in the solvent consisting of the supercritical fluid, into the recess 135; and a precipitation step of precipitating the metal from the metal compound introduced in the recess 135. Alternatively, the means for implementing the metal burying step may be an electroforming process as heretofore-known commonplace means. Particularly, in the above embodiment, a sidewall of the recess 135 is electrically-insulating aluminum oxide (alumina), and a bottom thereof is electrically-conductive aluminum, so that the second metal can be buried from the bottom of the recess 135 into the recess 135 in a bottom-up manner. Alternatively, the means for implementing the metal burying step may be a coating and filling process. This coating and filling process comprises coating and filling a metal paste containing a plurality of particles of the second metal, from the opening of the recess 135 into the recess 135.

Through the above production steps, the X-ray metal grating structure 1c having the configuration depicted in FIG. 12, including the X-ray absorptive portions 111c made of the second metal as an X-ray absorptive material buried in the recess 135, and the plugged-pore layer 134, is produced.

In the second embodiment, the first metal is a metal (including any alloy thereof) having an X-ray transmissive property, and the second metal is a metal (including any alloy thereof) having an X-ray absorptive property. Alternatively, the first metal may be a metal (including any alloy thereof) having, as the first property, a low phase-shifting property, i.e., a property capable of achieving only a relatively small phase-shifting amount, and the second metal may be a metal (including any alloy thereof) having, as the second property, a high phase-shifting property, i.e., a property capable of achieving a relatively large phase-shifting amount (a phase-shifting amount greater than that of the first metal).

The second production method for the X-ray metal grating structure 1c according to the second embodiment (including any modification thereof) has the same functions and advantage effects as those in the first embodiment. Further, in the second production method for the X-ray metal grating structure 1c according to the second embodiment, the X-ray absorptive portion 111c can be formed by burying an X-ray absorptive material in the recess 135, and the first region AR1 having the one or more pores PE can be relatively used as the X-ray transmissive portion 112c.

It should be noted that, although the X-ray metal grating structure 1 (1a, 1b, 1c) in the first and second embodiments (including any modification thereof) is a one-dimensional periodic structure, it is not limited thereto. For example, the X-ray metal grating structure 1 may be a two-dimensional periodic structured grating. For example, the two-dimensional periodic structured X-ray metal grating is configured such that dots indicative of a two-dimensional periodic structured member are arranged at even intervals of a given distance in two linear independent directions. Such a two-dimensional periodic structured X-ray metal grating can be formed by making a plurality of holes each having a high aspect ratio, in a planar surface in a two-dimensional period, or by standingly providing a plurality of columns each having a high aspect ratio, on a planar surface in a two-dimensional period. Further, a metal may be buried in these spaces in the same manner as that described above.

In the first and second embodiments (including any modification thereof), as a metal capable of allowing a plurality of pores to be formed therein by an anodic oxidation process or an anodic chemical conversion process, aluminum is used. Alternatively, the metal substrate 13a may be formed of any other suitable metal (including any alloy thereof). In addition to aluminum (Al) as mentioned above, examples of such a metal include tungsten (W), molybdenum (Mo), silicon (Si), gallium arsenide (GaAs) and indium phosphorus (InP). In the case where a process similar to an anodic oxidation process is implemented, there is a possibility that the metal substrate 13a is not oxidized depending on a material of the metal substrate 13a. In this case, the process is termed as "anodic chemical conversion process", instead of "anodic oxidation process".

In the case where the metal substrate 13a is formed of tungsten or molybdenum, a plurality of pores can be formed by an anodic oxidation process using a solution of nitric acid, oxalic acid or the like.

In the case where the metal substrate 13a is formed of silicon, when the metal substrate 13a is a P-type silicon (001) substrate, a plurality of pores can be formed by an anodic oxidation process using a mixed solution of hydrofluoric acid and methanol.

In the case where the metal substrate 13a is formed of gallium arsenide or and indium phosphorus, when the metal substrate 13a is an n-type gallium arsenide (001) substrate, a plurality of pores can be formed by an anodic oxidation process using a solution of ammonium hydroxide ($NH_4OH$). In this anodic oxidation process, the metal substrate 13a is immersed in the ammonium hydroxide solution while being irradiated with light and applied with a magnetic field, and then a voltage is applied thereto.

In the case where the metal substrate 13a is formed of any one of tungsten (W), molybdenum (Mo), silicon (Si), gallium arsenide (GaAs) and indium phosphorus (InP), the sealing process is implemented by subjecting the metal substrate 13a to heating treatment in an oxygen atmosphere. In this case, the pores PE can be sealed by means of volume expansion caused by oxidation.

In the first and second embodiments (including any modification thereof), the protective film 131 composed of a quartz film is preliminarily formed on the other principal surface to enable the pored layer 132 to be formed only in the one principal surface by an anodic oxidation process. Alternatively, the pored layer 132 may be formed in both of the one and the other principal surfaces to suppress a change in profile irregularity due to oxidation. In this case, after forming the pored layer 132 in both of the principal surfaces, a quartz layer may be formed on one of the principal surfaces to be not subjected to patterning, for example, by a TEOS-CVD process or the like, or a dry resist film or the like may be attached to the one principal surface, to thereby form the protective layer.

Next, two other embodiments of the present invention will be described.

(Third and Fourth Embodiments: Talbot Interferometer and Talbot-Lau Interferometer)

The X-ray metal grating structure 1 (1a, 1b, 1c) according to the above embodiments makes it possible to form a metal portion with a high aspect ratio, so that it can be suitably used in an X-ray Talbot interferometer and an X-ray Talbot-Lau interferometer. An X-ray Talbot interferometer and an X-ray Talbot-Lau interferometer each using the metal grating structure 1 will be described below.

Figure 14:
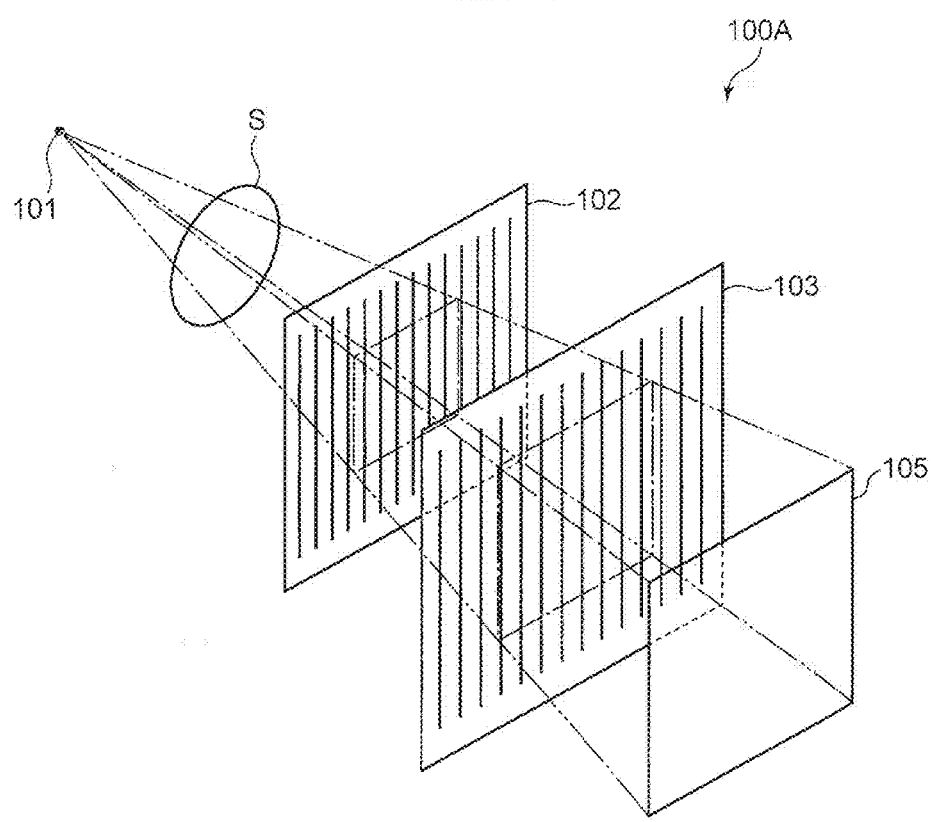
FIG. 14 is a perspective view depicting a configuration of an X-ray Talbot interferometer according to a third embodiment.
Figure 15:
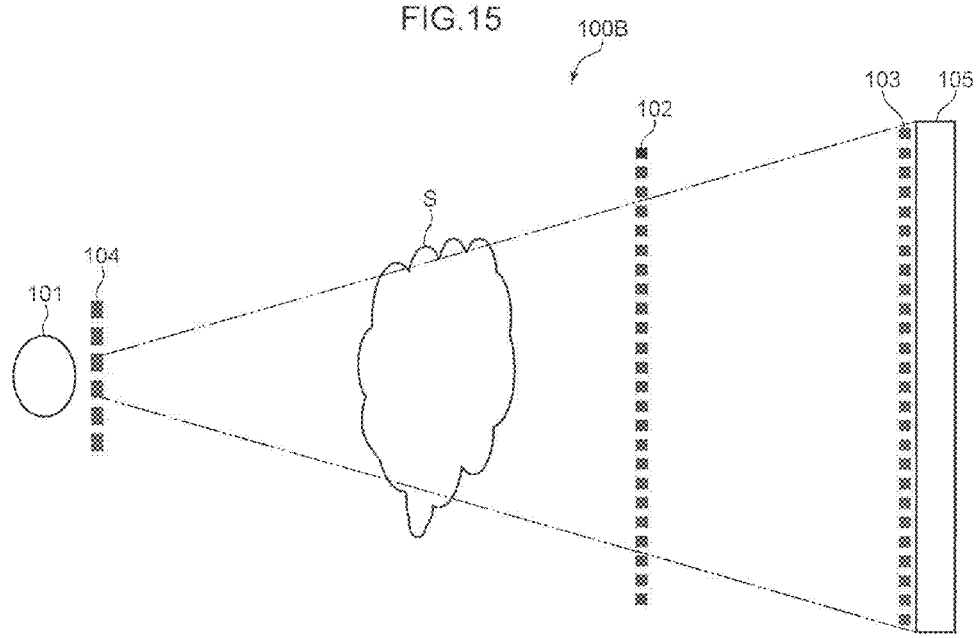
FIG. 15 is a perspective view depicting a configuration of an X-ray Talbot-Lau interferometer according to a fourth embodiment.

FIG. 14 is a perspective view depicting a configuration of an X-ray Talbot interferometer according to a third embodiment. FIG. 15 is a top view depicting a configuration of an X-ray Talbot-Lau interferometer according to a fourth embodiment.

As depicted in FIG. 14, the X-ray Talbot interferometer 100A according to the third embodiment includes: an X-ray source 101 which radiates X-rays having a given wavelength; a first diffraction grating 102 which is a phase type configured to diffract the X-rays radiated from the X-ray source 101; and a second diffraction grating 103 which is an amplitude type configured to diffract the X-rays diffracted by the first diffraction grating 102 to thereby form an image contrast, wherein the first and second diffraction gratings 102, 103 are set to satisfy conditions for constructing an X-ray Talbot interferometer. The X-rays having an image contrast generated by the second diffraction grating 103 are detected, for example, by an X-ray image detector 105 operable to detect X-rays. In the X-ray Talbot interferometer 100A, at least one of the first diffraction grating 102 and the second diffraction grating 103 is the X-ray metal grating structure 1 produced by any one of the X-ray metal grating structure production methods.

The conditions for constructing the Talbot interferometer 100A are expressed by the following formulas 1, 2. The formula 2 is based on an assumption that the first diffraction grating 102 is a phase-type diffraction grating.

$$I = \lambda/(a/(L+Z1+Z2)) \quad \text{formula (1)}$$

$$Z1 = (m+1/2) \times (d^2/\lambda) \quad \text{formula (2)}$$

, where: I denotes a coherence length; $\lambda$ denotes a wavelength of X-rays (generally, center wavelength); a denotes an aperture diameter of the X-ray source 101 in a direction approximately orthogonal to a diffraction member of a diffraction grating; L denotes a distance from the X-ray source 101 to the first diffraction grating 102; Z1 denotes a distance from the first diffraction grating 102 to the second diffraction grating 103; Z2 denotes a distance from the second diffraction grating 103 to the X-ray image detector 105; m denotes an integer; and d denotes a period of a diffraction member (a period of a diffraction grating, a grating constant, a distance between centers of adjacent diffraction members, or the pitch P).

In the X-ray Talbot interferometer 100A having the above configuration, X-rays are radiated from the X-ray source 101 toward the first diffraction grating 102. The radiated X-rays produce a Talbot effect through the first diffraction grating 102 to thereby form a Talbot image. The Talbot image forms an image contrast having moire fringes by an action received through the second grating 103. Then, the image contrast is detected by the X-ray image detector 105.

The Talbot effect means that, upon incidence of light onto the diffraction grating, an image identical to the diffraction grating (a self image of the diffraction grating) is formed at a position away from the diffraction grating by a certain distance, wherein the certain distance is called "Talbot distance L" and the self image is called "Talbot image". In the case where the diffraction grating is a phase-type diffraction grating, the Talbot distance L becomes Z1 (L=Z1) as expressed by the formula 2. The Talbot image appears as a reverted image when the Talbot distance is equal to an odd multiple of L (=(2 m+1), where each of L and m is an integer), and appears as a normal image when the Talbot distance is equal to an even multiple of L (=2 mL).

In the case, when a subject S is disposed between the X-ray source 101 and the first diffraction grating 102, the moire fringes are modulated by the subject S, and an amount of the modulation is proportional to an angle at which X-rays are bent by a refraction effect arising from the subject S. Thus, the subject S and an internal structure of the subject S can be detected by analyzing the moire fringes.

In the Talbot interferometer 100A configured as depicted in FIG. 14, the X-ray source 101 is a single spot light source. Such a single spot light source can be constructed by additionally providing a single slit plate formed with a single slit. X-rays radiated from the X-ray source 101 pass through the single slit of the single slit plate, and are radiated toward the first diffraction grating 102 through the subject S. The slit is an elongate rectangular opening extending in one direction.

On the other hand, as depicted in FIG. 15, a Talbot-Lau interferometer 100B is constructed in such a manner that it includes: an X-ray source 101; a multi-slit plate 104; a first diffraction grating 102; and a second diffraction grating 103. Specifically, the Talbot-Lau interferometer 100B is constructed in such a manner that it includes, in addition to the Talbot interferometer 100A depicted in FIG. 14, the multi-slit plate 104 having a plurality of slits formed in parallel relation, on an X-ray radiation side of the X-ray source 101.

The multi-slit plate 104 is a so-called zeroth grating, and may be the X-ray metal grating structure 1 produced by any one of the production methods for the X-ray metal grating structure 1. When the multi-slit plate 104 is produced by any one of the production methods for the X-ray metal grating structure 1, it becomes possible to transmit X-rays through the slit-shaped X-ray transmissive portion 112 (112a, 112c) while more reliably blocking X-rays by the slit-shaped X-ray absorptive portion 111 (111a, 111c), and thus more clearly discriminate between transmission and non-transmission of X-rays. This allows the multi-slit plate 104 to more reliably convert X-rays radiated from the X-ray source 101 into a multi-light source.

When the Talbot-Lau interferometer 100B is used, an X-ray dose irradiated toward the first diffraction grating 102 through the subject S is increased, as compared to the Talbot interferometer 100A, so that it becomes possible to obtain better moire fringes.

Next, yet another embodiment of the present invention will be described.

(Fifth Embodiment; X-Ray Imaging Device)

The X-ray metal grating structure 1 (1a, 1b, 1c) is utilizable in a variety of optical devices, and suitably used, for example, in an X-ray imaging device, because the X-ray absorptive portion 111 (111a, 111c) can be formed with a high aspect ratio. In particular, an X-ray imaging device using an X-ray Talbot interferometer is one phase contrast method designed to handle X-rays as waves and detect a phase shift occurring when X-rays penetrating through a subject to obtain a transmission image of the subject, so that it has an advantage of being able to expect to improve sensitivity about 1,000 times, as compared to an absorption contrast method designed to obtain an image by utilizing differences in magnitudes of X-ray absorption by a subject as contrast, thereby reducing an X-ray dose, for example, to $\frac{1}{100}$ to $\frac{1}{1000}$. In this embodiment, an X-ray imaging device equipped with an X-ray Talbot interferometer using the X-ray metal grating 1 will be described.

Figure 16:
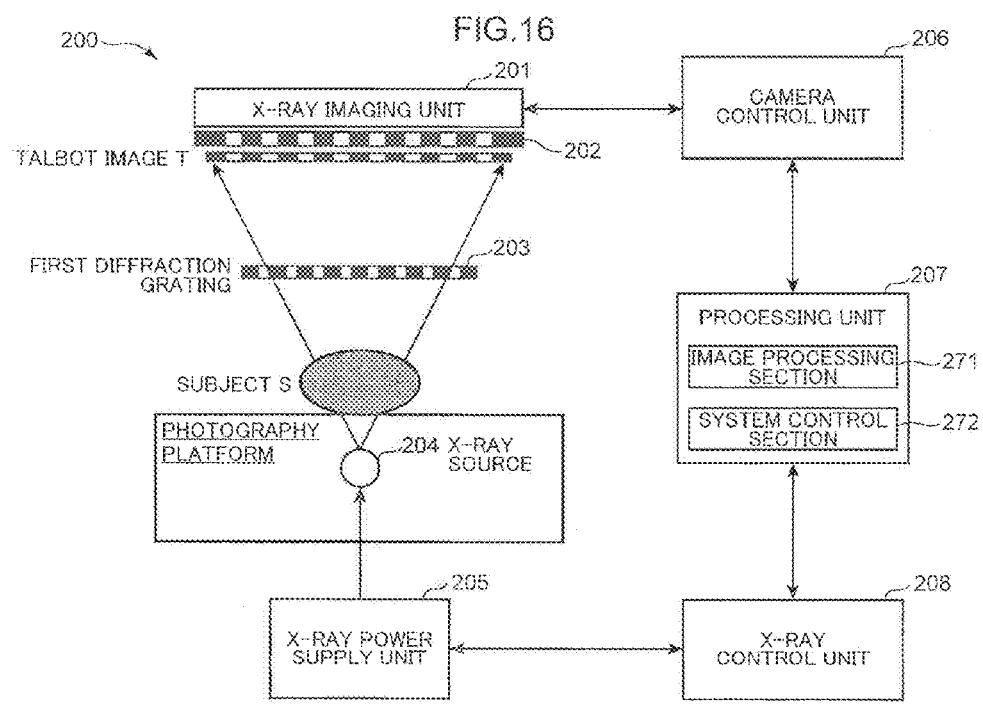
FIG. 16 is a schematic view depicting a configuration of an X-ray imaging device according to a fifth embodiment.

FIG. 16 is an explanatory diagram depicting a configuration of an X-ray imaging device according to a fifth embodiment. In FIG. 16, the X-ray imaging device 200 includes: an X-ray imaging unit 201; a second diffraction grating 202; a first diffraction grating 203; and an X-ray source 204. The X-ray imaging device 200 according to this embodiment further includes: an X-ray power supply unit 205 for supplying electricity to the X-ray source 204; a camera control unit 206 for controlling an imaging operation of the X-ray imaging unit 201; a processing unit 207 for controlling an overall operation of the X-ray imaging device 200; and an X-ray control unit 208 for controlling an electricity supply operation by the X-ray power supply unit 205 to thereby control an X-ray radiation operation by the X-ray source 204.

The X-ray source 204 is a device operable, in response to receiving electricity supplied from the X-ray power supply unit 205, to radiate X-rays toward the first diffraction grating 203. For example, the X-ray source 204 is a device configured such that a high voltage supplied from the X-ray power supply unit 205 is applied between a cathode and an anode, and electrons released from a filament of the cathode collide with the anode to thereby radiate X-rays.

The first diffraction grating 203 is a diffraction grating configured to produce a Talbot effect by X-rays radiated from the X-ray source 204. For example, the first diffraction grating 203 is a diffraction grating produced by any one of the production methods for the X-ray metal grating structure 1. The first diffraction grating 203 is constructed to satisfy conditions for producing a Talbot effect, and is a phase-type diffraction grating having a sufficiently coarse grating with respect to a wavelength of X-rays radiated from the X-ray source 204, for example, having a grating constant (a period of a diffraction grating) d of about 20 times or more of the wavelength of the X-rays. It should be understood that the first diffraction grating 203 may be an amplitude-type diffraction grating equivalent thereto.

The second diffraction grating 202 is a transmission and amplitude-type diffraction grating disposed at a position away from the first diffraction grating 203 approximately by a Talbot distance L, to diffract X-rays diffracted by the first diffraction grating 203. As with the first diffraction grating 203, the second diffraction grating 202 is also a diffraction grating produced by any one of the production methods for the X-ray metal grating structure 1.

The first and second diffraction gratings 203, 202 are set to satisfy conditions for constructing a Talbot interferometer expressed by the aforementioned formulas 1 and 2.

The X-ray imaging unit 201 is a device for imaging an image of X-rays diffracted by the second diffraction grating 202. For example, the X-ray imaging unit 201 is a flat panel detector (FPD) including a two-dimensional image sensor in which a thin film layer containing a scintillator for absorbing X-ray energy and emitting fluorescence is formed on a light receiving surface or an image intensifier camera including: an image intensifier unit for converting incident photons into electrons by a photoelectric surface, and after doubling the electrons by a micro-channel plate, causing the group of doubled electron to collide with a fluorescent material to generate fluorescence: and a two-dimensional image sensor for imaging output light from the image intensifier unit.

The processing unit 207 is a device for by controlling units of the X-ray imaging device 200 to thereby control the overall operation of the X-ray imaging device 200. For example, the processing unit 207 is constructed such that it includes a microprocessor and peripheral circuits thereof, and functionally has an image processing section 271 and a system control section 272.

The system control section 272 is operable to transmit and receive control signals with respect to the X-ray control unit 208 to thereby control an X-ray radiation operation of the X-ray source 204 through the X-ray power supply unit 205, and transmit and receive control signals with respect to the camera control unit 206 to thereby control an imaging operation of the X-ray imaging unit 201. Under control of the system control section 272, X-rays are irradiated toward the subject S. Then, a resulting image is taken by the X-ray imaging unit 201, and an image signal is input into the processing unit 207 via the camera control unit 206.

The image processing section 271 is operable to process the image signal generated by the X-ray imaging unit 201, and generate an image of the subject S.

An operation of the X-ray imaging device according to this embodiment will be described below. For example, a subject S is placed on a photography platform provided with the X-ray source 204 internally (or on the back thereof), and thereby disposed between the X-ray source 204 and the first diffraction grating 203. When a user of the X-ray imaging device 200 issues an instruction for imaging the subject S, from a non-depicted operation section, the system control section 272 in the processing unit 207 outputs a control signal to the X-ray control unit 208 for radiating X-rays to the subject S. According to the control signal, the X-ray control unit 208 instructs the X-ray power supply unit 205 to supply electricity to the X-ray source 204, and thus the X-ray source 204 radiates X-rays toward the subject S.

The radiated X-rays passes through the first diffraction grating 203 through the subject S, and is diffracted by the first diffraction grating 203, whereby a Talbot image T as a self image of the first diffraction grating 203 is formed at a position away from the first diffraction grating 203 by a Talbot distance L (=Z1).

The formed Talbot image T of X-rays is diffracted by the second diffraction grating 202, and an image of resulting moire fringes is formed. The image of moire fringes is imaged by the X-ray imaging unit 201 whose parameter such as exposure time is controlled by the system control section 272.

The X-ray imaging unit 201 outputs an image signal indicative of an image of moire fringes, to the processing unit 207 via the camera control unit 206. The image signal is processed by the image processing section 271 in the processing unit 207.

The subject S is disposed between the X-ray source 204 and the first diffraction grating 203. Thus, a phase of X-rays passing through the subject S is shifted from a phase of X-rays which does not pass through the subject S. As a result, X-rays entering the first diffraction grating 203 includes distortion in a wave front thereof, and a Talbot image T is deformed accordingly. Thus, the moire fringes of an image generated by overlapping the Talbot image T and the second diffraction grating 202 undergo modulation by the subject S, and an amount of the modulation is proportional to an angle at which the X-ray is bent by a refraction effect by the subject S. Therefore, the subject S and the internal structure of the subject S can be detected by analyzing the moire fringes. Further, the subject S may be imaged from different angles so as to form a tomographic image of the subject S by X-ray computed tomography (CT).

The second diffraction grating 202 in this embodiment is the X-ray metal grating structure 1 having the X-ray absorbable portions 111 with a high aspect ratio, according to each of the above embodiments. Thus, it is possible to obtain good moire fringes, thereby obtaining a highly-accurate image of the subject S.

In the above X-ray imaging device 200, a Talbot interferometer is composed of the X-ray source 204, the first diffraction grating 203, and the second diffraction grating 202. Alternatively, a Talbot-Lau interferometer may be constructed by additionally disposing the X-ray metal grating structure 1 according to the aforementioned embodiments as a multi-slit member on the X-ray radiation side of the X-ray source 204. Based on such a Talbot-Lau interferometer, an X-ray dose to be radiated to the subject S can be increased, as compared to the case where a single slit member is used. This makes it possible to obtain better moire fringes, thereby obtaining a further highly-accurate image of the subject S.

In the above X-ray imaging device 200, a subject S is disposed between the X-ray source 204 and the first diffraction grating 203. Alternatively, a subject S may be disposed between the first diffraction grating 203 and the second diffraction grating 202.

In the above X-ray imaging device 200, an image of X-rays is taken by the X-ray imaging unit 201, and electronic data of the image is obtained. Alternatively, an image of X-rays may be obtained by an X-ray film.

Next, yet another embodiment of the present invention will be described.

(Sixth Embodiment: Ultrasonic Probe and Production Method therefor)

An ultrasonic probe for use in non-destructive test (NDT) or medical procedure generally uses a single active element (piezoelectric element operable to perform both sending and receiving of a high-frequency acoustic wave). On the other hand, a phased array system includes a probe having a plurality of (e.g., 16 to up to 256) piezoelectric elements capable of generating pulses individually, wherein it is possible to arbitrarily change a propagation direction and a focus area of each ultrasonic wave generated from the plurality of piezoelectric elements by electrically controlling the ultrasonic waves individually, in terms of intensity, phase, etc.

A production method for such a phased array ultrasonic probe, using an ultrasonic probe production mold as a high-aspect ratio structure, will be described below.

Figure 17:
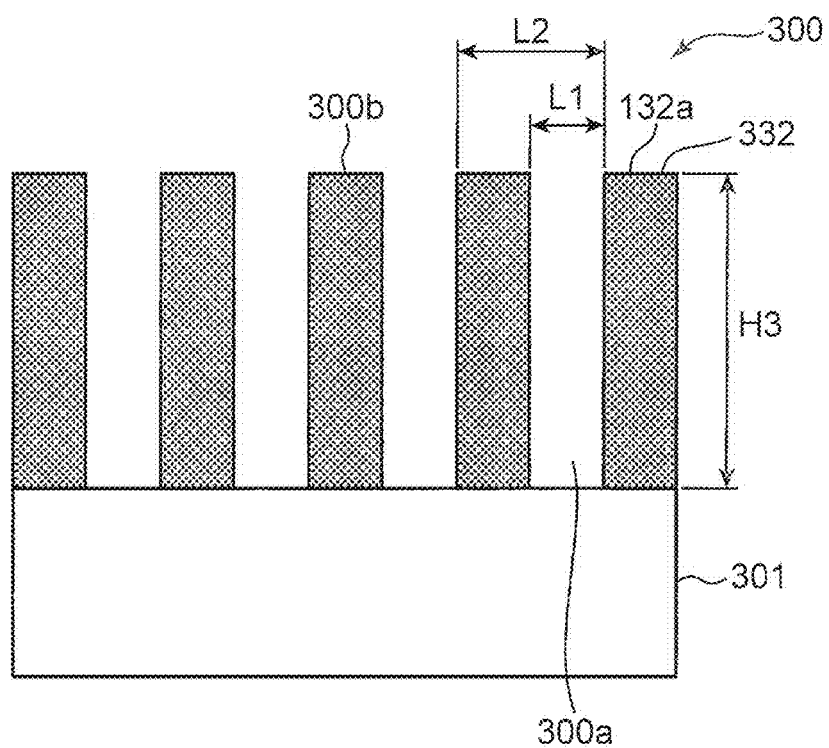
FIG. 17 is a sectional view depicting an ultrasonic probe production mold according to a sixth embodiment, which is one example of a high-aspect ratio structure produced by a high-aspect ratio structure production method.
Figure 18:
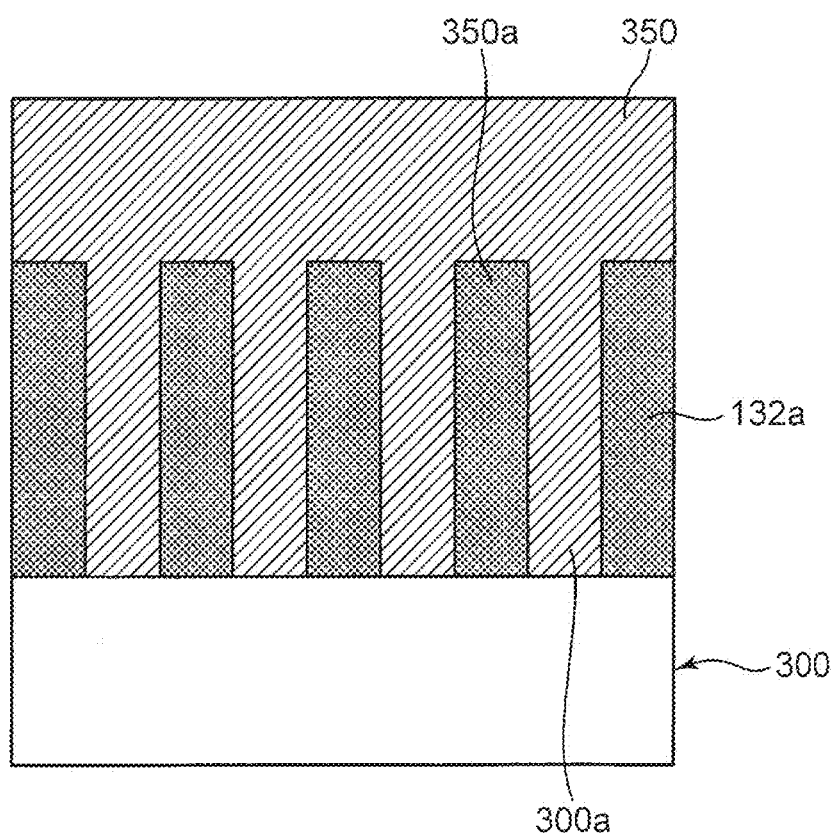
FIG. 18 is a sectional view illustrating a process for forming a metal mold using the ultrasonic probe production mold.
Figure 19:
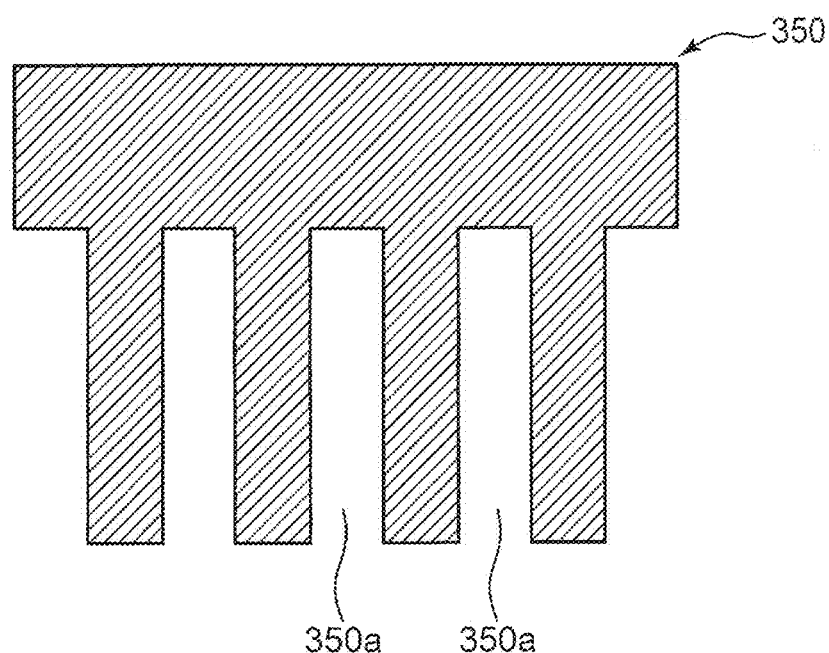
FIG. 19 is a sectional view depicting the metal mold in FIG. 18.
Figure 20:
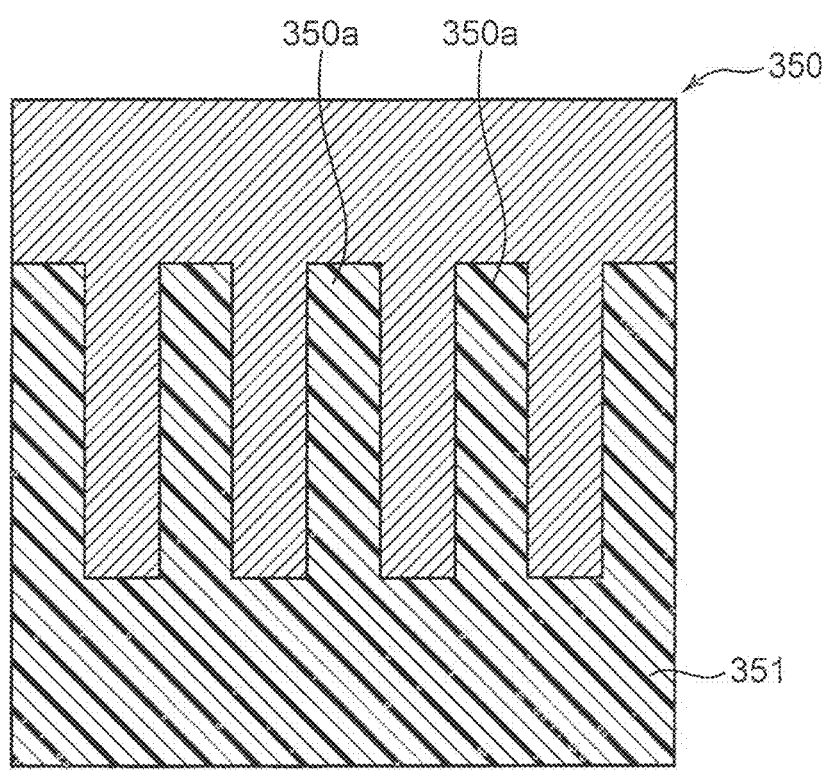
FIG. 20 is a sectional view illustrating a process for forming a resin mold using the metal mold in FIG. 18.
Figure 21:
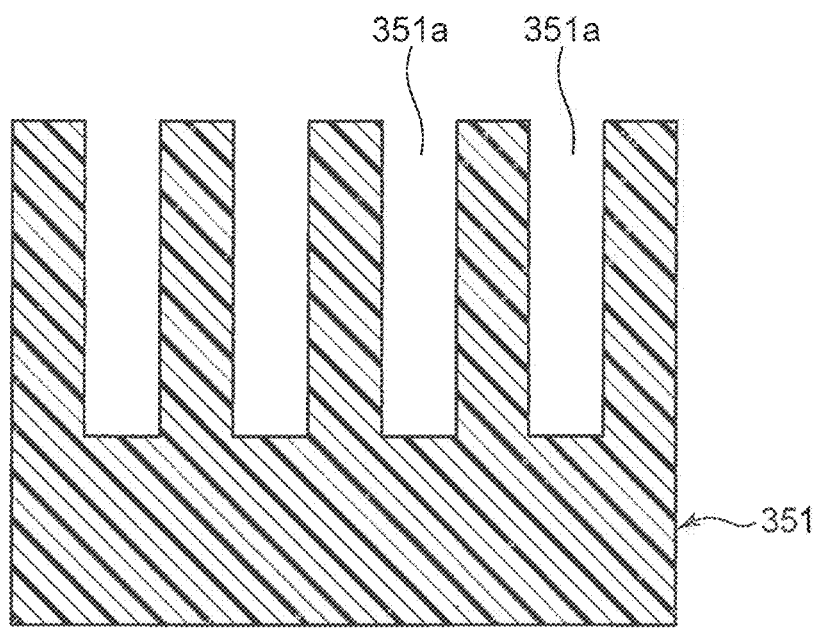
FIG. 21 is a sectional view depicting the resin mold in FIG. 20.
Figure 22:
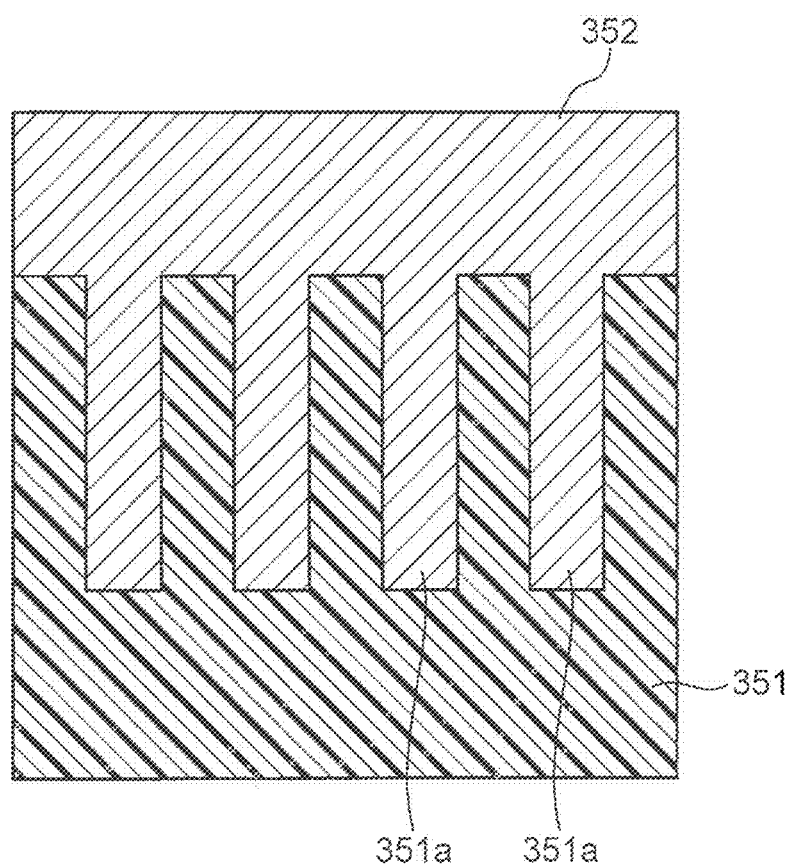
FIG. 22 is a sectional view illustrating a process for forming a lead zirconate titanate sintered body using the resin mold in FIG. 21.
Figure 23:
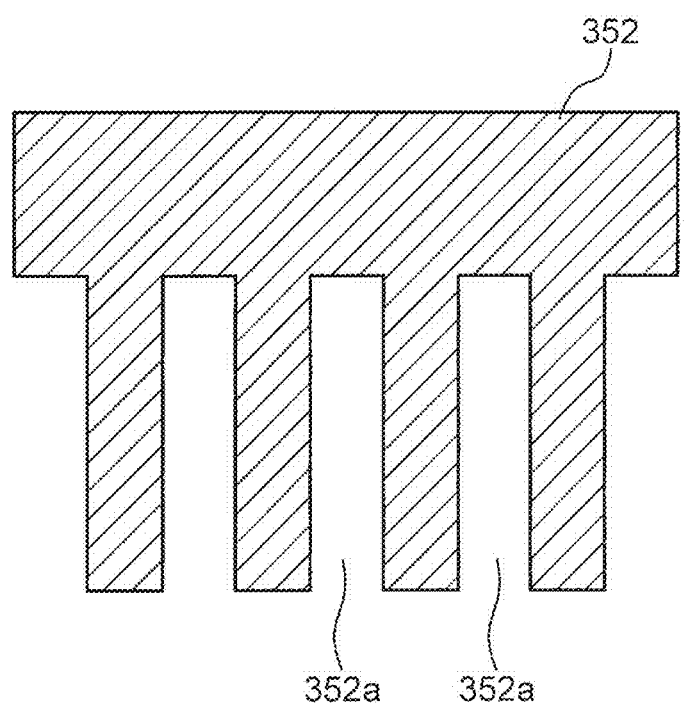
FIG. 23 is a sectional view depicting the lead zirconate titanate sintered body in FIG. 22.
Figure 24:
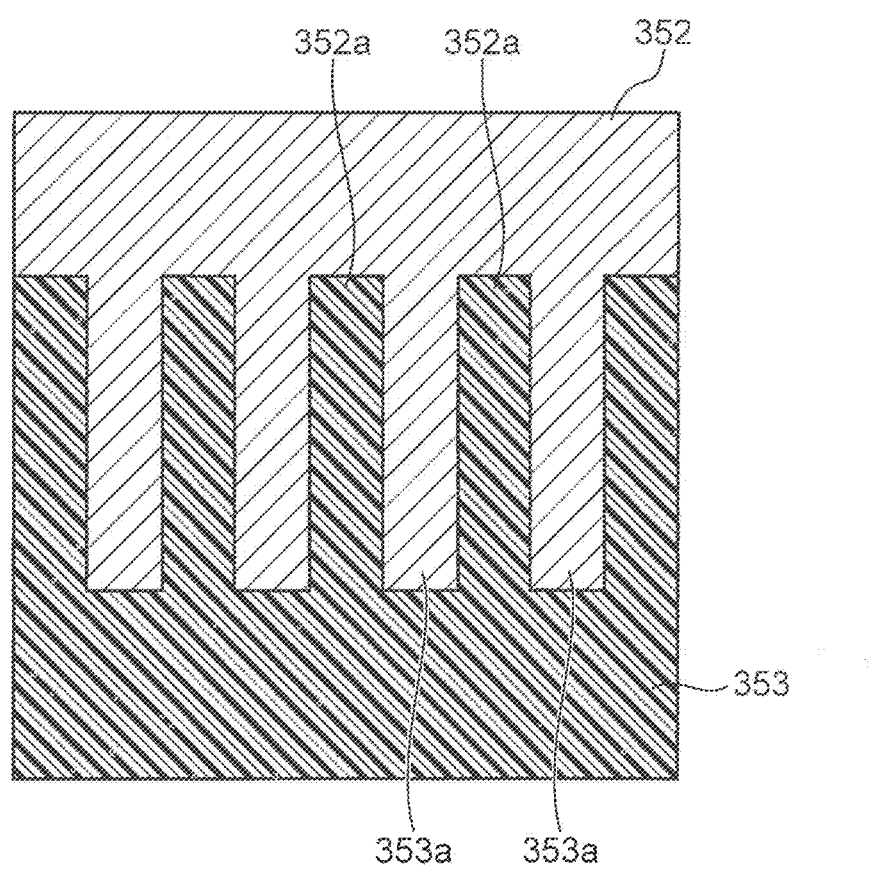
FIG. 24 is a sectional view depicting a state after filling a sintered body recess provided in the lead zirconate titanate sintered body in FIG. 23, with an epoxy resin.
Figure 25:
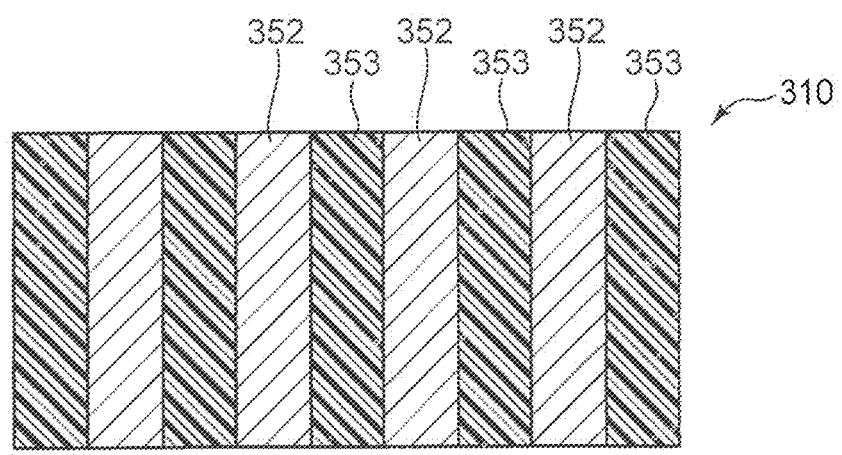
FIG. 25 is a sectional view depicting a substantial part of an ultrasonic probe formed from the state in FIG. 24.

FIG. 17 is a sectional view depicting an ultrasonic probe production mold according to a sixth embodiment, which is one example of a high-aspect ratio structure produced by the high-aspect ratio structure production method. FIG. 18 is a sectional view illustrating a process for forming a metal mold using the ultrasonic probe production mold. FIG. 19 is a sectional view depicting the metal mold in FIG. 18. FIG. 20 is a sectional view illustrating a process for forming a resin mold using the metal mold in FIG. 18. FIG. 21 is a sectional view depicting the resin mold in FIG. 20. FIG. 22 is a sectional view illustrating a process for forming a lead zirconate titanate sintered body using the resin mold in FIG. 21. FIG. 23 is a sectional view depicting the lead zirconate titanate sintered body in FIG. 22. FIG. 24 is a sectional view depicting a state after filling a sintered body recess provided in the lead zirconate titanate sintered body in FIG. 23, with an epoxy resin. FIG. 25 is a sectional view depicting a substantial part of an ultrasonic probe formed from the state in FIG. 24.

Through the same steps as those in the method for producing the X-ray metal grating structure 1a according to the first embodiment, an ultrasonic probe production mold 300 which is a one-dimensional high-aspect ratio structure, wherein a plurality of recesses 300a each having a width L1 of 15 μm and a depth H3 of 100 μm are serially arranged on a principle surface having a plugged-pore layer 332 in a substrate 301 made of aluminum, at a pitch distance L2 (=period: 30 μm), as depicted in FIG. 17.

Subsequently, as depicted in FIG. 18, an electroforming process is implemented using as a plating electrode, the substrate 301 defining a bottom of each of the recesses 300a of the ultrasonic probe production mold 300, so that the recess 300a is filled with nickel filler made of nickel and deposited until it has a thickness of 1 mm. Then, the ultrasonic probe production mold 300 is dissolved and removed by a phosphoric acid solution to prepare a metal mold 350 having a plurality of metal mold recesses 350a, as depicted in FIG. 19 (metal mold forming step).

Subsequently, as depicted in FIG. 20, the prepared metal mold 350 is filled with resin filler made of a resin material. For example, the resin material is an acrylic resin comprising polymethylmethacrylate (PMMA). A syrupy acrylic resin softened by heating is cast into each of the metal mold recesses 350a of the metal mold 350. The cast resin is cooled down to room temperature and hardened. Then, the resin material is released from the metal mold to prepare a resin mold 351 having a plurality of resin mold recesses 351a, as depicted in FIG. 21 (resin mold forming step).

Subsequently, as depicted in FIG. 22, each of the resin mold recesses 351a of the resin mold 351 is filled with a slurry containing lead zirconate titanate (PZT) particles. This slurry is adjusted using water and an organic binder. Then, the filled slurry is solidified by drying. Then, an ashing process using oxygen plasma is implemented to remove the resin mold 351 (FIG. 23). Then, the remaining solidified slurry is calcined at 500° C., and further burned at 1100° C. As a result of the burning, a lead zirconate titanate (PZT) sintered body 352 formed as a fine structure having a plurality of sintered body recesses (structure recesses) 352a is prepared to serve as a piezoelectric material, as depicted in FIG. 23 (fine structure forming step).

Each of the sintered body recesses 352a of the lead zirconate titanate sintered body 352 prepared in the above manner is filled with epoxy resin 353, as depicted in FIG. 24, and then respective base portions of the epoxy resin 353 and the lead zirconate titanate sintered body 352 are removed by grinding, as depicted in FIG. 25. In this way, an ultrasonic probe body 310 in which the epoxy resin 353 and the lead zirconate titanate sintered body 352 are alternately arranged to form an array is formed (an ultrasonic probe body forming step). Subsequently, electrodes are formed, respectively, on opposite surfaces of the ultrasonic probe body 310 to produce an ultrasonic probe.

As above, in the ultrasonic probe production mold 300 as a high-aspect ratio structure for use in the ultrasonic probe production method, each of the plurality of recesses 300a formed on one principle surface of the substrate 301 by a wet etching process has a side surface perpendicular to the one principle surface of the substrate 301. Further, in the ultrasonic probe production method, the ultrasonic probe body 310 is produced based on the ultrasonic probe production mold 300, so that it becomes possible to accurately arrange the lead zirconate titanate sintered body 352 and the epoxy resin 353 alternately to form an array, and produce the ultrasonic probe body 310 at low cost.

The specification discloses the aforementioned arrangements. The following is a summary of the primary arrangements of the embodiments.

A high-aspect ratio structure production method according to one aspect of the embodiments includes: a pore forming step of forming, in at least one principal surface of a given substrate, a plurality of pores each extending in a direction intersecting the principal surface; a resist layer forming step of forming a resist layer on the principal surface; a patterning step of subjecting the resist layer to patterning, and removing a part of the resist layer after being subjected to the patterning; a plugging step of plugging, among the plurality of pores, one or more pores formed in a first region from which the part of the resist layer has been removed in the patterning step; a resist layer removing step of removing the remaining resist layer left after the patterning step; and a recess forming step of forming, by a wet etching process, a recess in a second region from which the remaining resist layer has been removed in the resist layer removing step. Preferably, in the above high-aspect ratio structure production method, the resist layer forming step is a step of forming the resist layer using a dry film resist. Preferably, in the above high-aspect ratio structure production method, the plugging step is a step of plugging the pores by a sealing process using a sealing material. Preferably, in the above high-aspect ratio structure production method, an etchant for use in the recess forming step is set such that a reaching time required for the etchant entering from openings of the pores to reach bottoms of the pores becomes less than a dissolving time required for the etchant to dissolve partition walls formed between adjacent ones of the pores. More preferably, in the above high-aspect ratio structure production method, an etchant for use in the recess forming step is set such that a reaching time required for the etchant entering from openings of the pores to reach bottoms of the pores becomes less than a dissolving time required for the etchant to dissolve partition walls formed between adjacent ones of the pores by two digits or more (the reaching time required for the etchant entering from the openings of the pores to reach the bottoms of the pores)≤(the dissolving time required for the etchant to dissolve the partition walls formed between adjacent ones of the pores)/100).

In the above high-aspect ratio structure production method, during the wet etching process, the resist layer has already been entirely removed, wherein the one or more pores formed in the first region to be still left after the wet etching process are plugged, and the one or more pores formed in the second region from which the remaining resist layer has been removed after the plugging step are kept in an open state. Thus, even when the wet etching process is performed, an undercut phenomenon due to the resist layer never occurs, and an etchant can reach the bottoms of the pores in the second region, while dissolving the partition walls formed between adjacent ones of the pores. Thus, the high-aspect ratio structure production method makes it possible to produce a high-aspect ratio structure with a recess having a side surface approximately perpendicular to the one principal surface of the substrate by a wet etching process. As used therein, the term "aspect ratio" means a ratio of a thickness (depth) to a width of the recess (aspect ratio=depth/width).

In one specific embodiment, in the above high-aspect ratio structure production method, the pore forming step is a step of forming the plurality of pores by an anodic oxidation process or an anodic chemical conversion process.

The high-aspect ratio structure production method having this feature makes it possible to easily form, in the one principal surface of the substrate, a plurality of pores perpendicular to the one principal surface (a spreading plane of the one principal surface).

In another specific embodiment, in the above high-aspect ratio structure production method, the given substrate is formed of one selected from the group consisting of aluminum (Al), tungsten (W), molybdenum (Mo), silicon (Si), gallium arsenide (GaAs) and indium phosphorus (InP).

In the high-aspect ratio structure production method having this feature, the substrate is formed of one of the above materials, so that it becomes possible to easily form a plurality of pores perpendicular to the one principal surface, for example, by an anodic oxidation process or an anodic chemical conversion process.

In yet another specific embodiment, the above high-aspect ratio structure production method further includes an X-ray absorptive material burying step of burying an X-ray absorptive material capable of absorbing X-rays, in the recess.

In the high-aspect ratio structure production method having this feature, an X-ray absorptive portion can be formed by burying an X-ray absorptive material in the recess, and the first region having the one or more pores can be relatively used as an X-ray transmissive portion.

In still another specific embodiment, in the above high-aspect ratio structure production method, the X-ray absorptive material burying step includes burying a metal as the X-ray absorptive material by an electroforming process. More preferably, in this high-aspect ratio structure production method, the metal is one selected from the group consisting of gold (Au), platinum (Pt), rhodium (Rh) and iridium (Ir).

In the high-aspect ratio structure production method having this feature, a metal as the X-ray absorptive material is buried by an electroforming process, so that it becomes possible to bury the X-ray absorptive material easily and reliably.

In yet still another specific embodiment, in the above high-aspect ratio structure production method, the high-aspect ratio structure is an X-ray metal grating structure for use in an X-ray Talbot interferometer or an X-ray Talbot-Lau interferometer.

The high-aspect ratio structure production method having this feature makes it possible to produce a higher-performance X-ray metal grating structure serving as a zeroth grating, a first grating and a second grating for use in an X-ray Talbot interferometer or an X-ray Talbot-Lau interferometer.

In another further specific embodiment, in the above high-aspect ratio structure production method, the high-aspect ratio structure is an ultrasonic probe production mold for use in producing an ultrasonic probe.

The high-aspect ratio structure production method having this feature makes it possible to easily produce for use in producing an ultrasonic probe, at low cost.

An ultrasonic probe production method according to another aspect of the embodiments includes: a metal mold forming step of filling the recess of the aforementioned ultrasonic probe production mold, with a metal to form a metal mold having a metal mold recess; a resin mold forming step of filling the metal mold recess of the metal mold with a resin filler made of a resin material to form a resin mold having a resin mold recess; a fine structure forming step of filling the resin mold recess of the resin mold with a slurry containing a piezoelectric material to form a fine structure having a structure recess; and an ultrasonic probe body forming step of filling the structure recess of the fine structure with a synthetic resin to form an ultrasonic probe body in which a piezoelectric layer made of the piezoelectric material and a synthetic resin layer made of the synthetic resin are alternately arranged to form an array.

The ultrasonic probe production method having this feature makes it possible to form an ultrasonic probe body in which the piezoelectric layer and the synthetic resin layer are accurately arranged alternately to form an array, based on the ultrasonic probe production mold with the plurality of recesses each formed by a wet etching process to have a side surface perpendicular to the one principal surface of the substrate, and produce the ultrasonic probe body at low cost.

A high-aspect ratio structure according to yet another aspect of the embodiments includes: a substrate; and a grating formed in the substrate, wherein the grating has a plurality of convex portions formed to have a spatial periodicity, wherein each of the plurality of convex portions is provided with a plugging member plugging a plurality of pores formed therein in a thickness direction of the substrate. Preferably, in the above high-aspect ratio structure, the substrate is formed of the aluminum, and the recess is defined by aluminum oxide (alumina), wherein the plugging member is formed of a hydrate of aluminum oxide (alumina).

The high-aspect ratio structure can provide a high-aspect ratio structure. Particularly, when the above high-aspect ratio structure production method is used, this high-aspect ratio structure can be configured such that a recess relative to the convex portion has a side surface approximately perpendicular to one principal surface of the substrate, and produced at low cost.

This application is based on Japanese Patent application No. 2016-050408 filed in Japan Patent Office on Mar. 15, 2016, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A method for producing a high-aspect ratio structure, comprising:

a pore forming step of forming, in at least one principal surface of a given substrate, a plurality of pores each extending in a direction intersecting the principal surface;

a resist layer forming step of forming a resist layer on the principal surface;

a patterning step of subjecting the resist layer to patterning, and removing a part of the resist layer after being subjected to the patterning;

a plugging step of plugging, among the plurality of pores, one or more pores formed in a first region from which the part of the resist layer has been removed in the patterning step;

a resist layer removing step of removing the remaining resist layer left after the patterning step; and a recess forming step of forming, by a wet etching process, a recess in a second region from which the remaining resist layer has been removed in the resist layer removing step, wherein the pores in the second region are prevented from being plugged during the plugging step by the remaining resist layer.

2. The method as recited in claim 1, wherein the pore forming step is a step of forming the plurality of pores by one of an anodic oxidation process and an anodic chemical conversion process.

3. The method as recited in claim 1, wherein the given substrate is formed of one selected from the group consisting of aluminum (Al), tungsten (W), molybdenum (Mo), silicon (Si), gallium arsenide (GaAs) and indium phosphorus (InP).

4. The method as recited in claim 1, which further comprises an X-ray absorptive material burying step of burying an X-ray absorptive material capable of absorbing X-rays, in the recess.

5. The method as recited in claim 4, wherein the X-ray absorptive material burying step includes burying a metal as the X-ray absorptive material by an electroforming process.

6. The method as recited in claim 1, wherein the high-aspect ratio structure is an X-ray metal grating structure for use in one of an X-ray Talbot interferometer and an X-ray Talbot-Lau interferometer.

7. The method as recited in claim 1, wherein the high-aspect ratio structure is an ultrasonic probe production mold for use in producing an ultrasonic probe.

8. A method for producing an ultrasonic probe, comprising:

a metal mold forming step of filling the recess of the ultrasonic probe production mold as recited in claim 7, with a metal to form a metal mold having a metal mold recess;

a resin mold forming step of filling the metal mold recess of the metal mold with a resin filler made of a resin material to form a resin mold having a resin mold recess;

a fine structure forming step of filling the resin mold recess of the resin mold with a slurry containing a piezoelectric material to form a fine structure having a structure recess; and an ultrasonic probe body forming step of filling the structure recess of the fine structure with a synthetic resin to form an ultrasonic probe body in which a piezoelectric layer made of the piezoelectric material and a synthetic resin layer made of the synthetic resin are alternately arranged to form an array.

* * * * *